(12) United States Patent
Kilpatrick et al.

(10) Patent No.: US 12,384,997 B2
(45) Date of Patent: Aug. 12, 2025

(54) CELL CULTURE BIOREACTOR

(71) Applicant: ABEC, Inc., Bethlehem, PA (US)

(72) Inventors: Shane Alexander Jaques Kilpatrick, Mississauga (CA); Scott Raymond Pundsack, Georgetown (CA); Moin Ahmed, Waterloo (CA); Megan Logan, Elmira (CA)

(73) Assignee: ABEC, INC.

( * ) Notice: Subject to any disclaimer, the term of this patent is extended or adjusted under 35 U.S.C. 154(b) by 1074 days.

(21) Appl. No.: 17/280,727

(22) PCT Filed: Sep. 30, 2019

(86) PCT No.: PCT/CA2019/051397
§ 371 (c)(1),
(2) Date: Mar. 26, 2021

(87) PCT Pub. No.: WO2020/069607
PCT Pub. Date: Apr. 9, 2020

(65) Prior Publication Data
US 2021/0380922 A1     Dec. 9, 2021

Related U.S. Application Data

(60) Provisional application No. 62/856,315, filed on Jun. 3, 2019, provisional application No. 62/739,598, filed on Oct. 1, 2018.

(51) Int. Cl.
*C12M 1/00*      (2006.01)
*B01D 53/22*     (2006.01)
(Continued)

(52) U.S. Cl.
CPC .......... *C12M 29/10* (2013.01); *B01D 53/229* (2013.01); *B01D 63/0241* (2022.08);
(Continued)

(58) Field of Classification Search
None
See application file for complete search history.

(56) References Cited

U.S. PATENT DOCUMENTS 4,937,196 A    6/1990   Wrasidlo
5,366,625 A *  11/1994  Pedersen ............. B01D 63/026
                                              210/321.89
(Continued)

FOREIGN PATENT DOCUMENTS

CA      2566841 A1    11/2005
CN    103861455 A      6/2014
(Continued)

OTHER PUBLICATIONS

European Patent Application No. 19869945.6, European Search Opinion, dated Feb. 6, 2022.
(Continued)

*Primary Examiner* — William H. Beisner

(57) ABSTRACT

A cell culture bioreactor has perfusion membranes and gas transfer membranes or a gas phase in an extra-membrane space in contact with a film on the perfusion membranes. Gas transfer membranes may travel through the perfusion membranes or through the extra-membrane space. Examples with hollow fiber and flat sheet membranes are shown. One or more of the membranes optionally has a responsive surface, for example a thermo-responsive surface. In some examples, membranes are located in X-Y planes while the length of the reactor extends in a Z-direction.

15 Claims, 25 Drawing Sheets

(51) Int. Cl.
  *B01D 63/02* (2006.01)
  *B01D 69/06* (2006.01)
  *B01D 69/08* (2006.01)
  *C12M 1/02* (2006.01)
  *C12M 3/00* (2006.01)
  *C12N 1/20* (2006.01)

(52) U.S. Cl.
  CPC ............ *B01D 69/06* (2013.01); *B01D 69/08* (2013.01); *C12M 23/44* (2013.01); *C12M 27/00* (2013.01); *C12M 29/04* (2013.01); *C12M 29/16* (2013.01); *C12N 1/20* (2013.01); *B01D 2053/224* (2013.01); *B01D 2313/60* (2022.08)

(56) References Cited

U.S. PATENT DOCUMENTS

| | | | |
|---|---|---|---|
| 5,516,691 | A * | 5/1996 | Gerlach ................. C12M 23/16 435/297.1 |
| 5,622,857 | A | 4/1997 | Goffe |
| 5,658,797 | A * | 8/1997 | Bader ................... C12M 25/06 435/297.5 |
| 6,228,607 | B1 | 5/2001 | Kersten et al. |
| 7,862,718 | B2 | 1/2011 | Doyen et al. |
| 8,367,370 | B2 | 2/2013 | Wheeler et al. |
| 8,393,477 | B2 | 3/2013 | Kamleiter et al. |
| 9,284,531 | B2 | 3/2016 | Stachelscheid et al. |
| 2001/0042716 | A1 | 11/2001 | Iversen |
| 2002/0153299 | A1 | 10/2002 | Mahendran et al. |
| 2004/0229343 | A1* | 11/2004 | Husain ................. C02F 3/1273 210/615 |
| 2005/0003530 | A1 | 1/2005 | Gerlach |
| 2005/0142530 | A1 | 6/2005 | Galavotti |
| 2011/0124078 | A1* | 5/2011 | Edwards ............... C12M 29/16 435/243 |
| 2011/0159584 | A1 | 6/2011 | Gibbons |
| 2012/0132813 | A1 | 5/2012 | Baumfalk et al. |
| 2012/0149091 | A1 | 6/2012 | Wilkerson et al. |
| 2015/0017683 | A1* | 1/2015 | Abdullah ............... C12M 29/04 435/157 |
| 2016/0095969 | A1 | 4/2016 | Maurer et al. |
| 2016/0151535 | A1 | 6/2016 | Hoare et al. |
| 2016/0319234 | A1 | 11/2016 | Song et al. |
| 2018/0127705 | A1 | 5/2018 | Langenfeld et al. |
| 2019/0345433 | A1 | 11/2019 | Prabhudharwadkar et al. |

FOREIGN PATENT DOCUMENTS

| | | |
|---|---|---|
| EP | 0387975 A1 | 9/1990 |
| EP | 0419234 A2 | 3/1991 |
| EP | 2574664 A1 | 4/2013 |
| GB | 2477140 A | 7/2011 |
| JP | 2005333945 | 12/2005 |
| WO | 2005108549 A1 | 11/2005 |
| WO | 2008141935 A1 | 11/2008 |
| WO | 2010069319 A2 | 6/2010 |
| WO | 20140034146 A1 | 3/2014 |
| WO | 2021155469 A1 | 8/2021 |

OTHER PUBLICATIONS

International Patent Application No. PCT/CA2021/050124, International Preliminary Report on Patentability, dated Jul. 28, 2022.
Housler, Greggory J., et al., "Compartmental Hollow Fiber Capillary Membrane-Based Bioreactor Technology for In Vitro Studies on Red Blood Cell Lineage Direction of Hematopoietic Stem Cells", Tissue Engineering: Part C, vol. 18, No. 2, 2012. pp 133-142.
De Bartolo, Loredana et al., "Human hepatocyte functions in a crossed hollow fiber membrane bioreactor", Biomaterials 30 (2009) pp. 2531-2543.
Zhuang, Meiling et al., "Thermo-responsive poly(N-isopropylacrylamide)-grafted hollow fiber membranes for osteoblasts culture and non-invasive harvest", Materials Science and Engineering: C, vol. 55 (2015) pp. 410-419.
Ying, Lei et al., "Synthesis and Characterization of Poly(N-isopropylacrylamide)-graft-Poly(vinylidene fluoride) Copolymers and Temperature-Sensitive Membranes", Langmuir, 2002, 18 (16), pp. 6416-6423.
International Patent Application No. PCT/CA2019/051397, International Search Report and Written Opinion, dated Dec. 18, 2019.
International Patent Application No. PCT/CA2019/051397, International Preliminary Report on Patentability, dated Mar. 23, 2021.
Eghbali, Hadis et al., "Hollow fiber bioreactor technology for tissue engineering applications", International Journal of Artificial Organs, vol. 39, No. 1, Feb. 22, 2016, pp. 1-15.
Haigh, Jodie Nicole, "Melt Electrospinning Writing as a Method to Form Novel Hydrogel Architectures and Constructs", Masters of Science; Chemistry, Physics and Mechanical Engineering (CPME) Science and Engineering Faculty Queensland University of Technology, 2017, https://eprints.qut.edu.au/103849/1/Jodie_Haigh_Thesis.pdf.
Tripathi, Anurodh et al., "Synthesis of organic aerogels with tailorable morphology and strength by controlled solvent swelling following Hansen solubility", Scientific Reports, Feb. 1, 2018, vol. 8, No. 1, pp. 1-12.
Babgobin, Ravi, "Bubble-free oxygen and carbon dioxide mass transfer in bioreactors using microporous membranes", Masters of Engineering Science; The School of Graduate and Postdoctoral Studies, The University of Western Ontario, London, Ontario, Canada, Apr. 17, 2012, pp. 1-141, https://ir.lib.uwo.ca/etd/438/pdf.
Lo, Justin H. et al., "Gas Transfer in Cellularized Collagen-Membrane Gas Exchange Devices", Tissue Engineering, Part A, vol. 21, No. 15-16, 2015, pp. 2147-2155.
International Patent Application No. PCT/CA2021/050124, International Search Report and Written Opinion, dated May 20, 2021.
Canadian Patent Application No. 3,167,379, Office Action dated Aug. 4, 2023.
U.S. Appl. No. 17/168,085, Final Office Action dated Apr. 17, 2024.
U.S. Appl. No. 17/168,085, Office Action dated Aug. 2, 2023.
U.S. Appl. No. 17/168,085, Office Action dated Apr. 18, 2023.
U.S. Appl. No. 17/214,421, Office Action dated Mar. 1, 2024.
U.S. Appl. No. 17/214,421, Office Action dated Jun. 6, 2024.
European Patent Application No. 21750383.8, Partial Supplementary European Search Report dated Apr. 10, 2024.
European Patent Application No. 21750383.8, Extended European Search Report dated Nov. 13, 2024.
U.S. Appl. No. 17/168,085, Office Action dated Nov. 6, 2024.
Schmelzer, Eva et al., "Effect of Human Patient Plasma Ex Vivo Treatment on Gene Expression and Progenitor Cell Activation of Primary Human Liver Cells in Multi-Compartment 3D Perfusion Bioreactors for Extra-Corporeal Liver Support", Biotechnology and Bioengineering, vol. 103, No. 4, 2009.
Monga, Satdarshan P.S. and Jorg C. Gerlach, "Human fetal hepatocyte behavior in dynamic 3D perfusion culture bioreactors", Journal of Organ Dysfunction, 2007; 3: 183-192.
Gerlach, Jorg, C. et al. , "Bioreactor for a Larger Scale Hepatocyte in vitro Perfusion", Transplantation, vol. 58, No. 9, pp. 984-988, 1994.
Canadian Patent Application No. 3,167,379, Office Action dated Sep. 13, 2024.
U.S. Appl. No. 17/168,085, Final Office Action dated Nov. 6, 2024.
U.S. Appl. No. 17/214,421, Final Office Action dated Dec. 4, 2024.

* cited by examiner

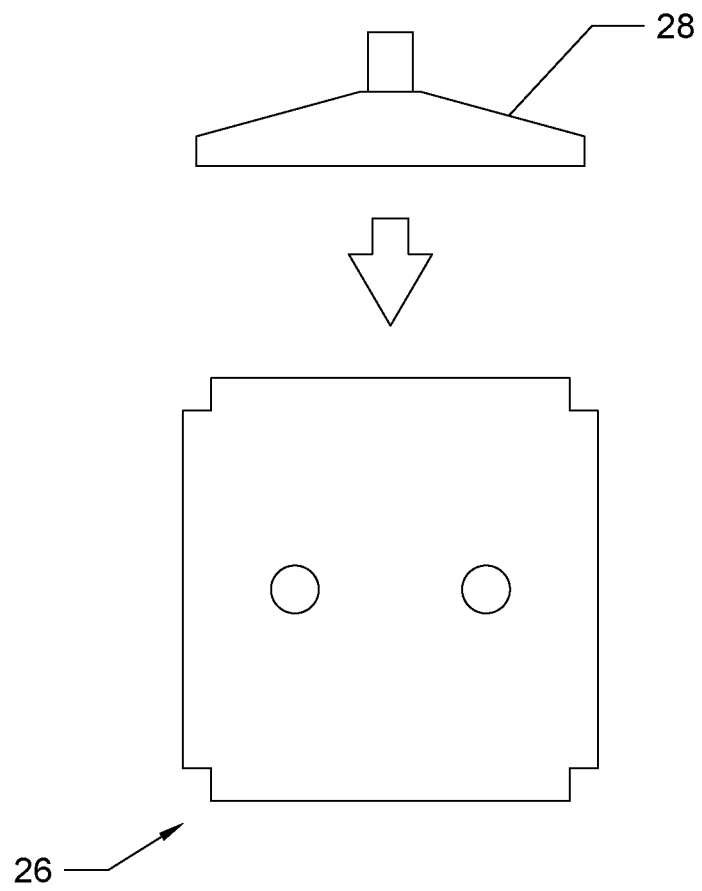
FIGURE 6A
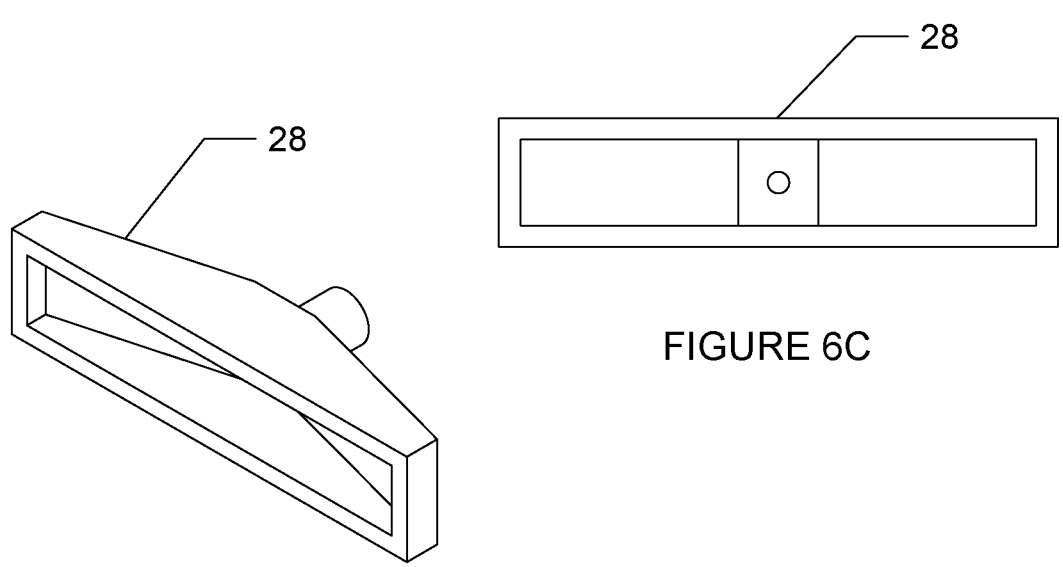
FIGURE 6B
FIGURE 6C

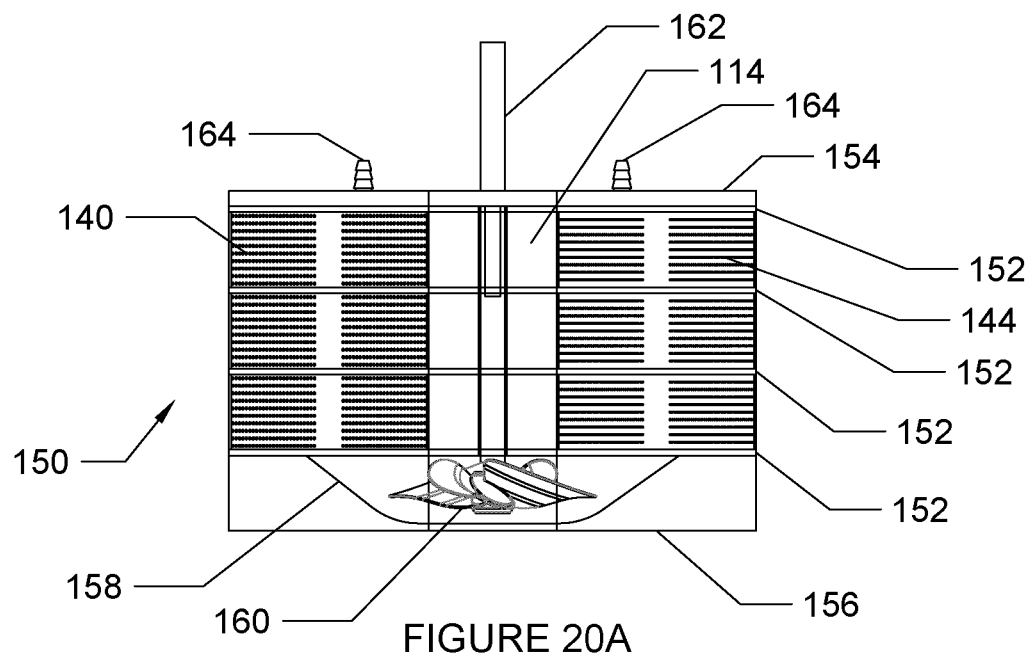
FIGURE 20A
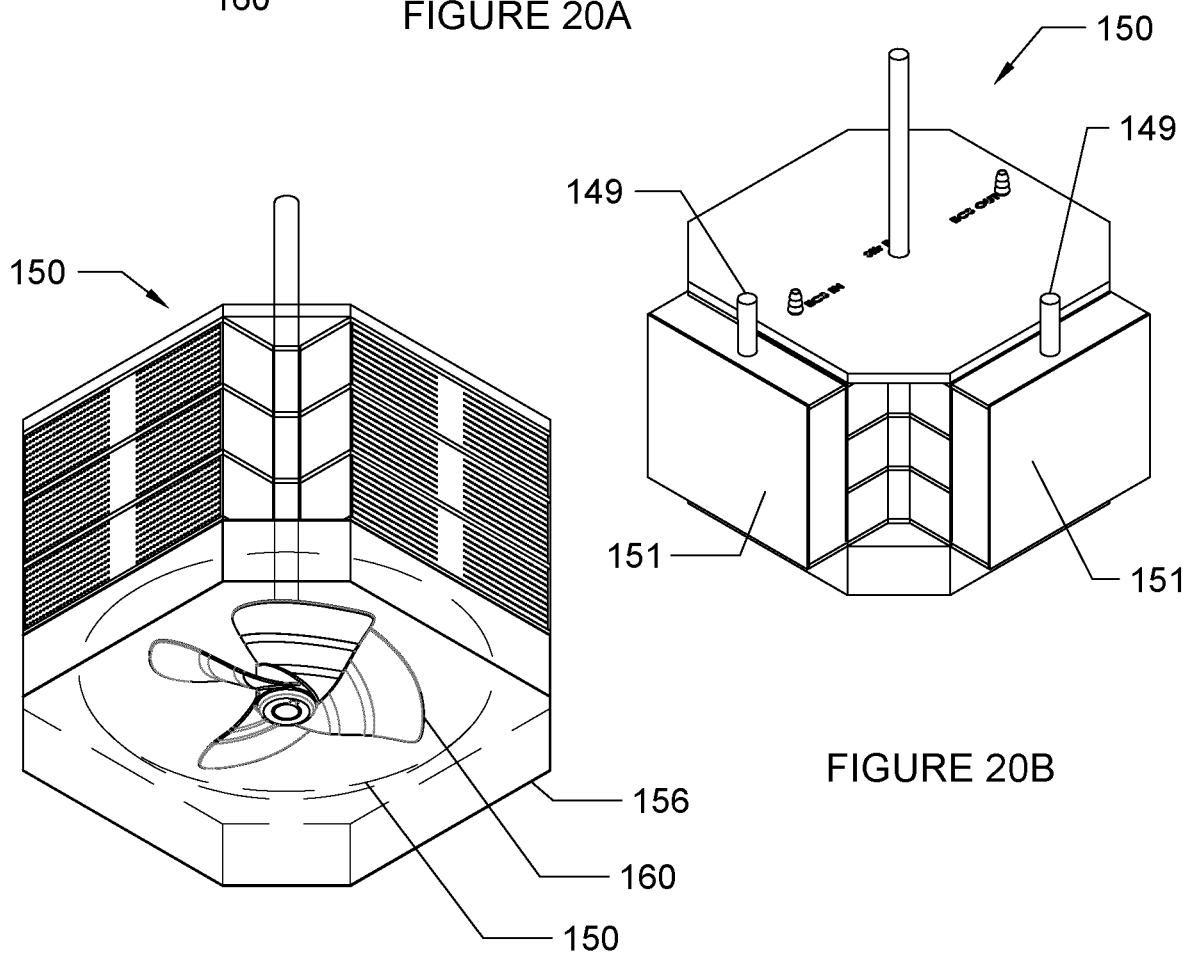
FIGURE 20B
FIGURE 20C

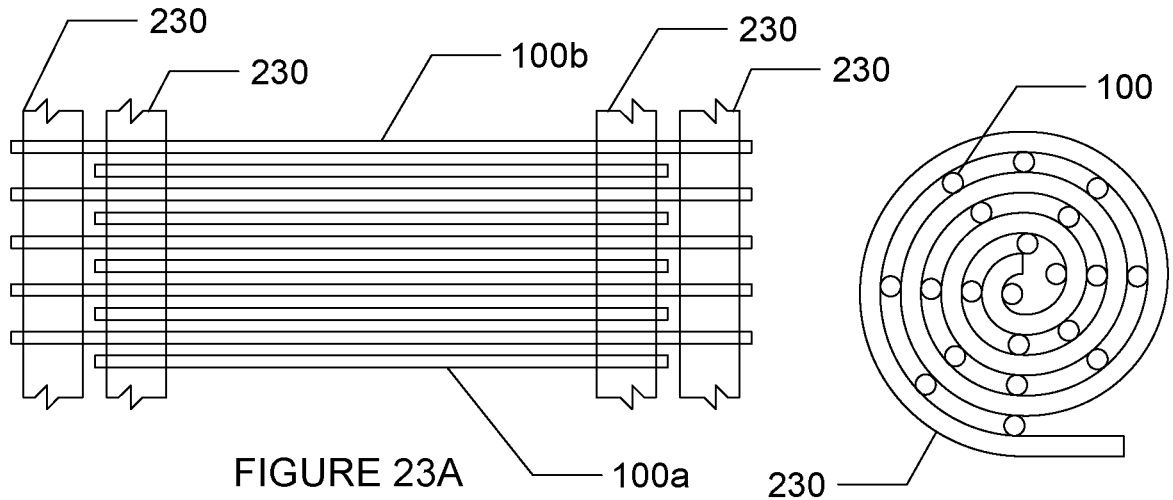
FIGURE 23A
FIGURE 23B
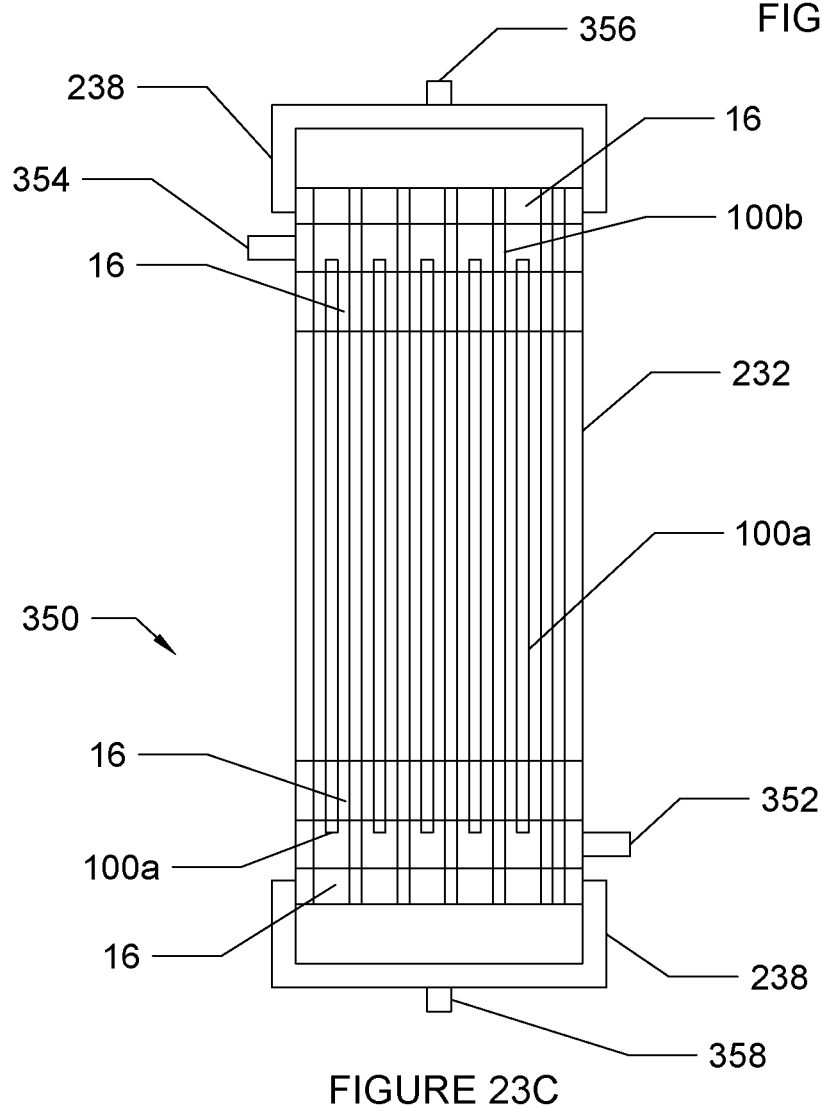
FIGURE 23C

CELL CULTURE BIOREACTOR

RELATED APPLICATIONS

This specification is a National Stage Entry of International Application No. PCT/CA2019/051397, filed Sep. 30, 2019, which claims the benefit of, and priority from, U.S. provisional application Nos. 62/739,598, Cell Culture Bioreactor, filed on Oct. 1, 2018, and 62/856,315, Sulfonated and Halide Membranes with Thermo-Responsive Surface Treatment, filed on Jun. 3, 2019, both of which are incorporated herein by reference.

FIELD

This specification relates to cell culture bioreactors and methods of culturing cells in a bioreactor.

BACKGROUND

The following is not an admission that anything discussed below is common general knowledge or citable as prior art.

The term "cell culture" is sometimes used to refer the culture of any cells and sometimes specifically to the culture of eukaryotes. In this specification, unless stated otherwise, cell culture includes the culture of any cells including a) eukaryotes, for example animal cells such as mammalian cells, b) non-eukaryotes such as bacteria, yeasts, fungi or protozoa (sometimes referred to as "microbial culture") and c) plant cells (sometimes referred to as "plant cell culture" or "tissue plant cell culture"). Further, cell culture as used in this specification, unless stated otherwise, includes growing cells for the purpose of obtaining the cells themselves and growing cells for the purpose of obtaining a product produced by the cells, for example a genetic material, protein, peptide or enzyme. This is in contrast to growing cells primarily for the purpose of consuming a pollutant as in wastewater treatment.

Many cells are anchorage dependent and grow primarily on a solid substrate. In some cell culture bioreactors, the substrate is provided by hollow fiber membranes. In some examples, a nutrient medium flows through the lumens of the hollow fiber membranes to provide a perfusion culture mode wherein nutrients diffuse through pores of the membranes to cells attached to the outside of the membranes.

INTRODUCTION

The following introduction is intended to introduce the reader to the detailed description to follow and not to limit or define any claimed invention.

This specification describes a cell culture bioreactor, methods of making a cell culture bioreactor and methods of culturing cells. The bioreactor defines a plenum. One or more types of membranes extend into, and optionally through, the plenum. Some of the membranes may be porous and/or some of the membranes may be dense-walled. The membranes may have various configurations, for example hollow fiber membranes or flat sheet membranes. The membranes thereby divide the plenum into an inner-membrane space and an extra-membrane space. Cells can be cultured in the extra-membrane space, for example in a liquid medium generally or completely filling the extra-membrane space (i.e. to the top of the reactor or to a free surface/headspace near the top of the reactor) or in a liquid film. The membranes are used to provide one or more nutrients to the cells. The nutrients may be a gas, a liquid or a solid dispersed or dissolved in a liquid. The cells may be anchorage dependent or not anchorage dependent. Anchorage dependent cells are optionally physically supported on the membranes, or alternatively or additionally supported on other material, such as micro-carriers, in the extra-membrane space. The design of the bioreactors may provide an alterative apparatus or culturing method, help to facilitate providing conditions suitable for the growth of cells through a large portion of the bioreactor or help to facilitate making a large bioreactor.

In some examples, a bioreactor includes perfusion membranes. The perfusion membranes are used to carry a liquid medium into or through their inner-membrane space. The perfusion membranes may be generally straight and extending in a direction that is generally parallel with other perfusion membranes, or between two closely (i.e. 10 mm or less) spaced planes that are generally parallel with other perfusion membranes and optionally also gas transfer membranes. The plenum extends in a direction oblique to, for example generally perpendicular to, the orientation (meaning either the parallel direction or the direction of the closely spaced planes) of the perfusion membranes. For example, the plenum can extend in the oblique direction by 50% or more, 100% or more or 200% or more of the length (or average length or mean length) of the perfusion membranes. In at least some cases, the overall volume of the bioreactor, in particular the extra-membrane space, can be increased without increasing the length of the perfusion membranes. For a given membrane type, increasing the length of the perfusion membranes can interfere with maintaining acceptable conditions throughout the extra-membrane space.

In some examples, a cell culture bioreactor has gas transfer membranes that are close to, or in direct contact with, liquid medium in the extra-membrane space. In this way, a supply of oxygen within the gas transfer membranes in a gas phase (as opposed to dissolved oxygen) can be brought near the cells. For example, the gas transfer membranes may traverse the plenum and define at least some boundaries of the extra-membrane space. Alternatively, the gas transfer membranes may traverse the plenum within perfusion membranes that define at least some boundaries of the extra-membrane space. In this case, the gas transfer membranes are still close, for example within 10 mm of, parts of the extra-membrane space that are more than 10 mm from the periphery of the plenum.

In some examples the bioreactor may have both perfusion membranes and gas transfer membranes. The gas transfer membranes may be oriented oblique to, for example generally perpendicular to, the perfusion membranes. Optionally, the gas transfer membranes may be longer than the perfusion membranes, for example in terms of mean length or average length. The ability of gas transfer membranes to transfer acceptable amounts of a nutrient, for example oxygen, to a fluid in the extra-membrane space appears to extend over lengths greater than the length of conventional perfusion membranes. Accordingly, arranging the bioreactor such that the lengths of the gas transfer and perfusion membranes are at least partially independent facilitates making the overall size of the extra-membrane space larger. In some examples, the gas transfer membranes are 30 cm or more or 40 cm or more in length.

In some examples, the bioreactor includes one or more types of membranes and a mixer. The mixer may be, for example a paddle mixer. The mixer is not used in combination with a bubble sparger near the mixer to oxygenate the liquid media as in a conventional bioreactor, but to re-suspend settled cells, homogenize liquid in the extra-membrane space and/or disturb quiescent boundary layers around the membranes. Optionally, the membranes are arranged so as to provide channels oblique to the membranes for mixing flows.

In some examples, the bioreactor is made up of stackable sub-units. The sub-units contain gas transfer and/or perfusion membranes. The sub-units are stacked in a direction oblique to the membranes. The sub-units can thereby be assembled into bioreactors of various sizes. Despite the variable size of the bioreactors, the length of the membranes does not change.

In some examples, a bioreactor has a liquid film on the outside of one or more membranes. The liquid films surrounds cells which may be anchored to the cells. The cells may be nourished by way of perfusion through the membrane and by a transfer of oxygen from a gas phase in the extra-membrane space through an outer surface of the liquid film.

In some examples, wherein the cell culture bioreactor is optionally used to grow anchorage dependent cells, a membrane incudes a responsive material. The responsive material can be activated to help remove cells from the membranes. In some examples, a membrane comprises a responsive hydrogel, for example a temperature responsive hydrogel, for example on an outer surface of the membrane or on an outer surface of a supporting structure for the membrane. In some examples, the membrane (or a separation layer of the membrane) is made of cellulose acetate or another polymer such as PS, PES, cellulose acetate, cellulose, PVDF or by the responsive polymer itself. In some examples, the responsive hydrogel is PNIPAAm (alternatively abbreviated as NIPAM); poly(2-oxazoline) (including for example poly(2-substituted-2-oxazoline), poly(2-isopropyl-2-oxazoline), poly(2-ethyl-2-oxazoline)m poly(2-nonyl-2-oxazoline) or co-polymers thereof); or, poly(oligoethylene glycol methacrylate) (POEGMA). In some examples, the responsive polymer forms a gel, for example a hydrogel.

In some examples of a process, a bioreactor for example as described above is operated with cells growing on or in a responsive polymer. Perfusion is provided by way of a nutrient medium supplied to the inside of the membrane. In a growth phase, nutrients flow through the responsive polymer (and optionally any intervening supporting or separating layers) to the cells. In a harvesting phase, the responsive polymer is expanded by a change in one or more environmental factors, such as temperature, pH or ionic strength, in the bioreactor. Detachment of the cells is optionally enhanced by one or more of movement of a membrane; a flow of liquid, bubbles or two-phase fluid past the membrane; or, a flow of liquid, bubbles or two-phase fluid through the membrane.

In some examples, a cell culture bioreactor has a membrane and POEGMA or poly(2-oxazoline). In some examples a cell culture bioreactor has perfusion including a flow of nutrients though a responsive layer attached to a membrane. In some examples a membrane has cellulose acetate or a cellulose supporting layer and POEGMA.

In some examples a tissue culture bioreactor has perfusion and/or gas transfer with a tissue supporting membrane.

In some examples, two or more of the aspects or features described above or in other parts of this specification or the figures are combined into a bioreactor or process.

BRIEF DESCRIPTION OF FIGURES

FIG. 6A shows some steps in a process of forming a single cartridge reactor (as shown in FIG. 7) involving attaching a fluid connector to the intermediate assembly of FIG. 5; FIGS. 6B and 6C are isometric and bottom views of the fluid connector of FIG. 6A.

FIG. 20A is a quarter side view of parts of a reactor including three of the modules of FIG. 19; FIG. 20B is an isometric view of the reactor of FIG. 20A; FIG. 20C is an isometric view of the parts of the reactor of FIG. 20A.

FIGS. 23A and 23B show steps in making another reactor; FIG. 23C shows a cross section of the finished reactor.

Figure 1:
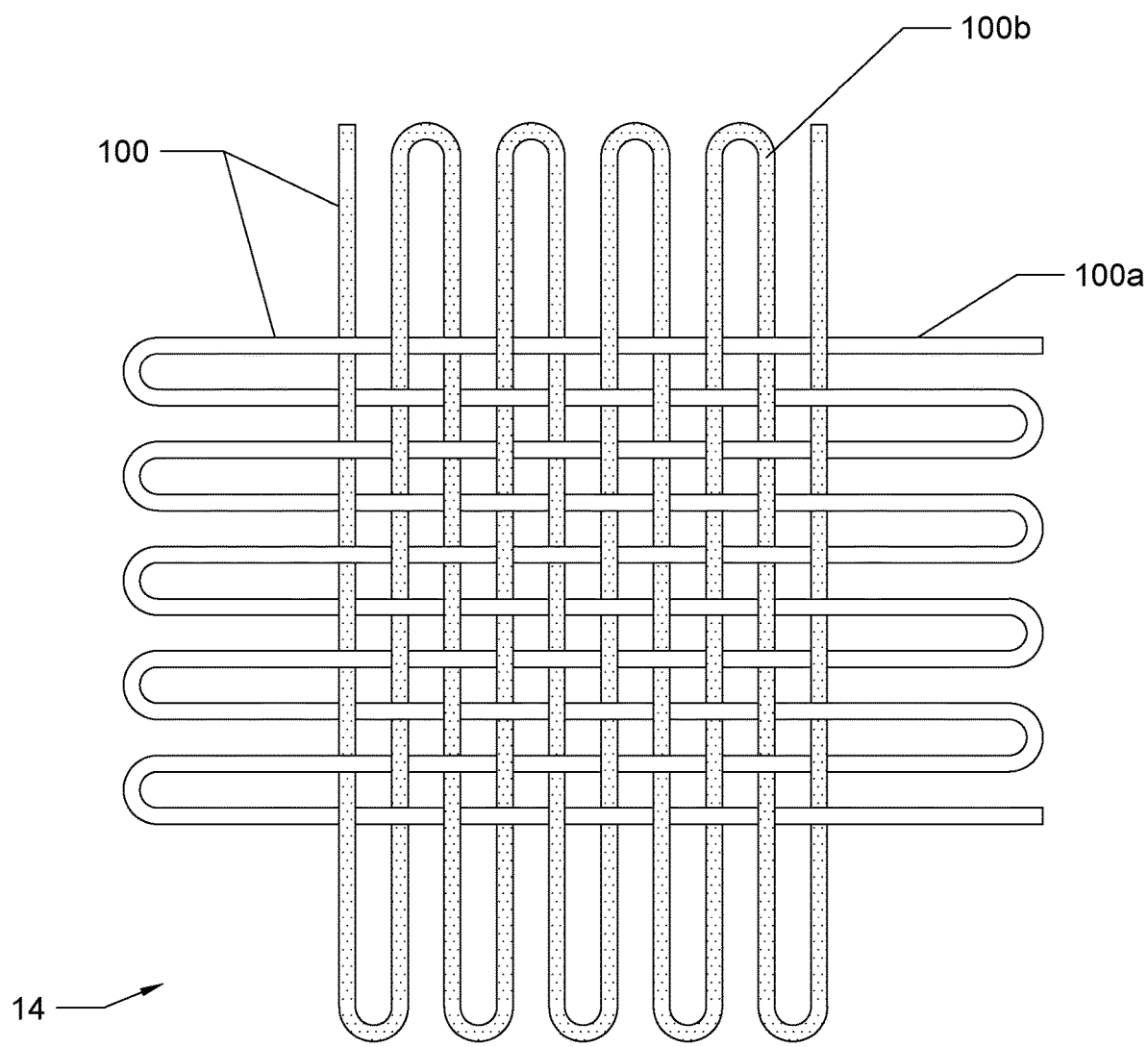
FIG. 1 is a plan (top) view of an assembly of hollow fiber membranes including liquid and gas carrying membranes.

All of the Figures are schematic and not drawn to scale.

DETAILED DESCRIPTION

In this specification, the words "reactor" and "bioreactor" may be used interchangeably. Both words refer to reactors used for cell culture meaning, as discussed in the background section, the growth of eukaryotic, non-eukaryotic or plant cells. The cells may be grown for the purpose of producing the cells themselves or for the purpose or producing a compound produced by the cells. A cell product compound may be recovered in some cases after it is expressed outside of the cells while the cells are growing in the bioreactor or, in other cases, by removing the cells from the bioreactor and then harvesting the cell product compound. Various examples of bioreactors and methods are described but features can be selected from multiple examples and combined to produce other bioreactors or methods.

The bioreactor defines a plenum in which the cells grow. In the examples described herein, this plenum also contains one or more membranes. Each membranes separates, in some cases but for pores or other openings of the membrane material, an inner-membrane space from an extra-membrane space. In the case of hollow fiber membranes, these spaces may alternatively be call the capillary space and the extra-capillary space. The bioreactor, or specifically the plenum, as a whole thereby has an inner-membrane space volume and an extra-membrane volume. The cells grow generally in the extra-membrane space.

Nutrients can be gaseous, liquid or solids dissolved or dispersed in a liquid medium. A gaseous nutrient, for example oxygen, can be delivered in a gaseous medium or dissolved in a liquid medium. A liquid medium can be supplied through the inner-membrane space or the extra-membrane space. Similarly, a gaseous medium may be supplied through the inner membrane space or the extra-membrane space.

The cells typically grow within the extra-membrane space. The extra-membrane space typically contains a first liquid media in which the cells are immersed and grow. The first liquid media may be present as a film over the membranes (and cells attached to the membranes) or generally throughout the extra-membrane space. For example, the first liquid media may fill the extra-membrane space entirely or to a free surface typically located above the membranes and defining the start of a headspace in the reactor. In some examples (and unless stated otherwise), a first liquid media is provided directly (i.e. not through a membrane) to the extra-membrane space.

One or more membranes, which may be called perfusion membranes, are used to carry a second liquid media through the inner-membrane space. Although the word "perfusion" may suggest the delivery of oxygen as well as dissolved or dispersed nutrients, in this specification the second liquid media is not required to contain material amounts of oxygen when gas transfer membranes are also present. However, adding oxygen to the second liquid media is not prohibited. For example, the second liquid media may be substantially (i.e. 80% or more) saturated with oxygen before it enters the perfusion membranes. The second liquid media may be the same as the first liquid media, at least before one or both of the media is modified by the cells. Alternatively, the second liquid media may be different from the first liquid media. For example, in perfusion the second liquid media can contain one or more nutrients that are consumed by the cells. These nutrients are at a greater concentration in the second liquid media than the concentration of the same nutrients in the first liquid media. The nutrients travel through the membranes into the first liquid media. While the word "perfusion" can be used to refer specifically to the diffusion of nutrients, in this specification the word "perfusion" can include diffusion but is not intended to exclude all bulk flow of the second liquid media or other transport mechanisms and the term "perfusion membranes" is similarly not so limited. However, in most examples (and unless stated otherwise) the perfusion membranes are not expected to operate primarily as pressure driven membranes used for filtration or the bulk transfer of a liquid media.

Perfusion membranes may have pores in the range of microfiltration or less (i.e. smaller), for example in the range of microfiltration, ultrafiltration or nanofiltration. Pores in the ultrafiltration range, i.e. with a molecular weight cut-off (MWCO) in the range of 5,000 to 200,000 Da, are typical. However, where the retention of small proteins or other compounds in the first liquid media is desirable, the pore size may extend down into the loose nanofiltration range, for example down to 1,000 Da. Conversely, where protein exclusion is not a significant concern, pore sizes may extend upward into the tight microfiltration range, for example up to 0.1 or 0.2 micrometers. The primary material in a perfusion membrane may be, for example, cellulose acetate, polysulfone, polyether-sulfone, or another biocompatible polymer. At least when in use, the pores of the diffusion membranes are substantially (i.e. but for defective pores) filled with a liquid.

In some example, one or more membranes, which may be called gas transfer membrane, are used to carry a gaseous media through the inner-membrane space. The gaseous media may be, for example, air, modified (i.e. oxygen enriched) air, oxygen, or a customized mix of gasses. The gaseous media may contain a gaseous nutrient, for example oxygen. Optionally, the gaseous nutrient diffuses into the first liquid media either by way of diffusion (or dissolution-diffusion or other transport mechanism) through the dense material of the gas transfer membrane itself. The dense material (i.e. the normally occurring solid phase of the polymer material not intentionally made more porous) typically has inter-molecular spaces that are large enough to pass oxygen (or other nutrient gas molecules) but not large enough to permit a bulk flow of water. Alternatively, the gaseous nutrient diffuses into the first liquid media across a gas-liquid interface formed between gas-filled pores of the gas transfer membrane and the first liquid medium. Although the gas transfer membrane may be porous, and the pores might be large enough in other contexts to permit a bulk flow of water, pores of the gas transfer membrane are filled with a gas and, due to surface effects such as the hydrophobicity of the membrane material and the surface tension of the first liquid media, do not admit the first liquid media. The pores therefor do not provide bulk liquid flow and pores that become filled with a liquid are considered defective. In most cases (and unless stated otherwise) the gas transfer membranes are not expected to operate primarily as pressure driven membranes used for creating bubbles in a liquid media.

Gas transfer membranes may have a dense wall of a highly oxygen-permeable material, for example of polymethylpentene (PMP) or a silicone such as polydimethylsiloxane (PDMS), an asymmetric wall with a dense region, or a porous wall. Gas transfer membranes with a porous wall are typically made of a melt-spun polymer, which may be inherently hydrophobic and/or treated to make it more hydrophobic, to help inhibit wetting of the pores. The melt-spun polymer can be stretched or otherwise treated during the spinning process to produce small pores.

The form of membranes described herein, whether gas transfer membranes or perfusion membranes, may be for example hollow fiber, flat sheet or tubular. Hollow fiber membranes have a round cross-section typically with a small diameter, for example 4 mm or less or 2 mm or less, and are flexible. The wall of a hollow fiber membrane is typically made of a single polymer (including polymer blends) although some hollow fiber membranes with a supporting structure of a textile (i.e. braided) or cast tube are available. The inner-membrane space may be referred to as a lumen or capillary space and the outer membrane space may be referred to as an extra-capillary space. Tubular membranes also have a round cross-section but typically with a larger diameter, for example 5 mm or more. Tubular membranes are usually supported on a textile tube and are generally rigid. Flat sheet membranes are typically formed by casting membrane material onto a textile, for example a woven or non-woven sheet. The resulting sheets are flexible and, despite the word "flat" can be bent into curved shapes such as spirals. Flat sheet membranes do not inherently define an inner membrane space but can be made into envelopes, pockets or other structures that define inner membrane and outer membrane spaces.

In some examples, a bioreactor has gas transfer membranes that are directly in contact with the first liquid media, which contains the cells growing in the bioreactor. Alternatively, gas transfer membranes can be provided within the inner-membrane space of one or more perfusion membranes. In this configuration the gas transfer membranes are still close to, for example within 10 mm of, the first liquid media and at least some of the cells.

Most of the bioreactors described herein extend materially in at least one direction oblique, for example perpendicular, to the flow of a nutrient (gas or liquid) through a membrane in the bioreactor. In this way, the size of the bioreactor can be increased without increasing the effective length of a membrane. In some examples, gas transfer membranes are oriented obliquely to perfusion membranes and the reactor also extends in a third direction obliquely to both the gas transfer and perfusion membranes.

Optionally, a bubble sparger or aerator, or mechanical mixer such as a rotating inclined plate, may be provided in a bioreactor outside of the membranes. The mixer can be used to keep cells in suspension, homogenize reactor contents and/or disturb boundary layers around membranes. The aerator or sparger can be used to provide bubbles in liquid (i.e. first liquid media) on the outside of the membranes to help remove cells, for example by action of the bubbles against the cells, by shaking the membranes, or by creating turbulence or other liquid movement in the bioreactor. In other examples, a sweep fluid can be provided through the bioreactor to help remove cells. In other examples, a bulk flow fluid can be pushed through the membranes (i.e. through the pores of the membranes from the inside to the outside) to help remove cells. Two or more of these methods may be combined, optionally in further combination with the use of responsive materials.

In any of the reactors described herein, the membranes (and other surfaces exposed to the cells) may be optionally coated with one or more responsive materials or not coated with any responsive materials. When the bioreactor is optionally used to grow anchorage dependent cells, the membranes preferably include a responsive material. The responsive material can be activated to help remove cells from the membranes.

Generally speaking, responsive materials have linear chains that may exist in an expanded or collapsed form. The linear chains may be free linear chains. Alternatively, the linear chains may be interconnected, for example cross-linked, to form a gel such as a hydrogel. When the responsive material is attached to or part of a surface, the surface (or at least the responsive part of it) may collapse or swell depending on changes in one or more environmental factors. Cells may be cultured in one state of the responsive material, for example its collapsed state, and released from another state of the responsive material, for example its expanded state.

A responsive material may be attached to a membrane, be incorporated with a membrane forming material, or provide a membrane (or at least the separating layer of a supported membrane) itself. The membrane may be, for example, a hollow fiber membrane (optionally called "fiber" for brevity), tubular membrane or a flat sheet membrane. The membrane may have pores, for example, in the microfiltration, ultrafiltration or nanofiltration range.

With unsupported membranes, for example hollow fiber membranes, the pores may be asymmetric such that one side of the membrane has the controlling pore size. The responsive material may be attached to either the controlling or non-controlling side of the membrane. Alternatively, the responsive material may be part of the membrane, for example by co-polymerization with a conventional membrane forming material.

In some cases, a flat sheet membrane, tubular membrane or hollow fiber membrane may have a supporting layer and a separation layer. The supporting layer may be, for example, a paper or fabric sheet, a paper or fabric tube, or a hollow knitted or braided tube. The separation layer is typically polymeric and contains the controlling pores, for example in the microfiltration, ultrafiltration or nanofiltration range. The responsive material may be attached to the supporting layer or to the separation layer, may provide the separation layer itself, or may be part of a separation layer that also incudes another conventional membrane polymer. In a cell culture bioreactor with perfusion, the flowing liquid nutrient solution (i.e. the second liquid media) and/or gas and the growing cells are typically on opposite sides of the membranes.

In some examples, a responsive polymer is attached directly to a supporting layer to produce a membrane without a separate non-responsive membrane layer. In this case, the responsive polymer, typically in its collapsed state, provides the controlling pore size or an analogue of the controlling pore size determined by the ability of a gas or nutrients to diffuse (or otherwise travel) through the responsive polymer. Optionally, the supporting layer has small openings, for example it may have pores in the microfiltration range or less, such that the membrane as a whole is still a microfilter (or less) even with the responsive polymer in an expanded state.

The controlling pore size side of a membrane (including the separation layer of a membrane with a supporting layer regardless of the exact configuration of the pores) may be in contact with either (i) the flowing nutrient solution (i.e. the second liquid media) and/or gas or (ii) the cells.

In a membrane supported cell culture bioreactor with perfusion, cells grow on a surface of the membrane. A fluid, which may be liquid, gas or two-phase, flows past the opposite surface of the membrane. Nutrients from a liquid and/or oxygen or other components of a gas travel through the membrane, for example by diffusion, to the cells. Waste or respiration products of the cells may also travel back through the membrane to the fluid. In some cases, during a growth phase, cells adhere to the membrane. During a harvesting phase for these cells, a change in one or more environmental factors, such as temperature, pH or ionic strength, causes an optional responsive material to go through a conformational change. For example, free linear chains on the surface of a membrane may swell or elongate. A hydrogel on the surface of a membrane may swell or dehydrate. Some or all of the cells are thereby detached from the membranes. Detachment may be spontaneous or aided, for example, by one or more of a flow of fluid (liquid, gas, bubbles or two-phase flow) on the cell side or by a bulk flow of fluid through the membrane to the cell side.

Various methods of attaching responsive polymers to a substrate, or otherwise providing membranes comprising responsive polymers, are described below. The substrate made be a solid surface (for example a sheet, molding or hollow fiber), a porous membrane surface (for example a hollow fiber membrane or a flat sheet membrane, optionally with pores in the microfiltration, ultrafiltration or nanofiltration range) or a membrane supporting material (for example a non-woven fabric, a woven fabric or filter paper). The attachment may be, for example, by way of chemical bond or adsorption. All of the publications mentioned herein are incorporated by reference.

Zhuang et. al., *Thermo-responsive poly(N-isopropylacrylamide)-grafted hollow fiber membranes for osteoblasts culture and non-invasive harvest*, Materials Science and Engineering C 55 (2015) 410-419, describes the preparation of thermo-responsive cellulose acetate hollow fiber membranes prepared via free radical polymerization in the presence of cerium (IV). In this method, poly(N-isopropylacrylamide) (PNIPAAm) is covalently grafted to the cellulose acetate of the membranes. This method can be adapted to graft PNIPAAm to cellulose or cellulose acetate flat sheet membranes or membrane supporting materials.

European Patent Application publication EP 2574664 A1, Method for preparation a thermosensitive coating substrate, the substrate with a thermosensitive coating and its application, Utrata-Wesolek et. al. describes the immobilization of a thermo-sensitive polymer from a group of homo- and copolymers of 2-substituted-2-oxazoline onto a modified surface consisting of a non-organic base substrate, preferably glass or silicon. This method can be adapted to immobilize the poly(2-oxazoline) onto a substrate (optionally a microporous substrate) of glass fibers, for example a braid fiberglass hollow fiber or a knitted or woven fiberglass fabric sheet or a fiberglass filter paper.

Ying et al., *Synthesis and Characeterization of Poly(N-isopropylacrylamide)-graft-Poly(vinylidene fluoride) Copolymers and Temperature-Sensitive Membranes*, Langmuir, 2002, 18 (16), pp. 6416-6423, describes molecular modification of ozone-pretreated poly(vinylidene fluoride) (PVDF) via thermally induced graft copolymerization with N-isopropylacrylamide (NIPAAM) in N-methyl-2-pyrrolidone solution to produce a NIPAAM-g-PVDF copolymer. Microfiltration membranes were made from the graft co-polymer by the phase inversion method.

Another method of attaching a responsive polymer to a cellulose acetate membrane (for example a microfiltration, ultrafiltration or nanofiltration flat sheet or hollow fiber membrane) or to a cellulose substrate for a flat sheet or tubular membrane (for example a microfiltration, ultrafiltration or nanofiltration membrane) is derived from US Patent Application Publication Number US 2016/0151535, Poly (Oligoethylene Glycol Methacrylate) Hydrogel Compositions, and Methods of Use Thereof, Hoare et al., published on Jun. 2, 2016, which is incorporated herein by this reference to it. Using the methods described therein to create aldehyde-functionalized POEGMA (POA) and hydrazide-functionalized POGMA (POH), or purchasing similar commercially POA and POH compounds, i.e. from Sigma Aldrich, a hydrogel is attached to a cellulose or cellulose acetate substrate (for example a membrane or membrane supporting fabric) by a layer by layer assembly of POEGMA. The substrate may be, for example, a cellulose acetate hollow fiber membrane, a cellulose acetate separation layer of a supported (i.e. flat sheet or tubular) membrane, or a cellulose acetate or cellulose supporting layer of a supported membrane.

POEGMA-hydrazide and POEGMA-aldehyde polymers (i.e. POA and POH) prepared from Example 1 of US Patent Application Publication Number US 2016/0151535 are first dissolved in 4% (w/v) phosphate buffered saline (PBS) solutions, or commercially available POA and POH solution is obtained and optionally diluted. Samples of substrate are then dipped in the polymer solutions by completely submerging the substrate in the solution. POA can optionally be used in the first dipping step. After 4 h of gentle shaking (about 30 rpm) at room temperature, the substrate samples are removed from the solution and washed twice with PBS. Afterwards, the samples are dried overnight at ambient conditions (about 23 degrees C. and about 30% relative humidity). Subsequently, the dried samples are dipped in the 4% (w/v) POH solution for another 4 hours and then washed and dried using the same procedure outlined above. Optionally, multiple dipping cycles can be used to provide more hydrogel mass (i.e. POEGMA adsorption or grafting). The polymers adsorb to the cellulose or cellulose acetate membranes or fibers and covalent bond formation occurs to form a thin hydrogel film on the substrate surface. Alternatively, in place of dipping, POH and/or POA can be coated, for example with a coating knife, on the surface of the membrane or substrate and allowed to absorb. Excess POH and/or POA, if any, can be scraped away. In another alternative, POH and/or POA are adsorbed onto the membrane of substrate by forming a bag containing the POH and/or POA of non-porous sheets compressed around the membrane or substrate. Optionally, one side of the membrane or substrate can be blocked during POH and/or POA adsorption by glycerin or a gel, for example a glycerin-containing gel, or other blocking substance.

The outer surfaces of a flat sheet membrane assembly may include a responsive material. In one example, a responsive material such as poly(2-oxazoline) is attached to the outside of a fiberglass fabric sheet or directly onto a fiberglass 3D spacer. In another example, a responsive material such as POEGMA is attached, for example by adsorption of one or more of its pre-polymers (POA or POH), to a silk, cellulose or cellulose acetate fabric sheet or paper or to a cellulose acetate membrane coating on a supporting structure. In other examples a responsive material such as NIPAM is attached to a cellulose acetate membrane coating on a supporting structure. In a case wherein the responsive material is attached to a fabric or paper sheet, there can optionally be a membrane coated on the inside of the fabric or paper sheet to provide a controlling pore size (i.e. the orientation of the flat sheet membrane is reversed compared to a typically flat sheet membrane filter) or the responsive material may provide the controlling pore size without another membrane on the inside.

FIGS. 1-8 show examples of cell culture bioreactors with hollow fiber membranes 100 that may be assembled in the form of a single cartridge reactor 10 or a multi-cartridge reactor 12. The height of the multi-cartridge reactor 12 (the direction perpendicular to the hollow fiber membranes 100, for example perpendicular to the circular cross-section in FIG. 8A) can be 50% or more, 100% or more or 200% or more of the length of the hollow fiber membranes 100 (or the longer or shorter of them, or the perfusion membranes 100a, if they have different sizes). This usefully allows the size of the multi-cartridge reactor 12 to be large for a given length of hollow fiber membranes 100, for example the perfusion membranes 100a, and optionally easy to manufacture in a variety of reactor volumes. However, the single cartridge reactor 10 is also useful, for example in testing new processes or materials.

The hollow fiber membranes 100 include perfusion membranes 100a and gas transfer membranes 100b. In an example, perfusion (i.e. liquid carrying) membranes 100a are cellulose acetate based, have a MWCO of 50 kDa, an OD of 0.8 mm and an ID of 0.5 mm and are optionally coated with a responsive polymer. The gas transfer (i.e. gas carrying) membranes 100b are PMP, have a pore size of less than 0.2 micrometers or are dense-walled, have an OD of 0.4 mm and an ID of 0.3 mm. Alternatively, other membranes may be used.

By orienting the gas transfer membranes 100b obliquely to (i.e. perpendicular to) the perfusion membranes 100a, the gas transfer membranes 100b can be added without increasing the potting density of the perfusion membranes 100a, which is calculated as the cumulative cross-sectional area of perfusion membranes 100a as a percentage of the cross-sectional area of the potting material 16 immediately surrounding the perfusion membranes 100a. Further, though not shown in the example of FIG. 1, one of the types of hollow fiber membranes 100, typically the gas transfer membranes 100b, can be longer than the other. In the example shown, the gas transfer membranes 100b are woven with the perfusion membranes 100a. In a woven structure, the hollow fiber membranes 100 of the warp and weft do not need to be of equal sizes. A smaller, more flexible, hollow fiber membrane may undulate around a larger, more rigid, hollow fiber membrane. For example, the gas transfer membranes 100b may have an outside diameter of less than 0.6 mm, or be a multi-filament, while the perfusion membranes 100a may have an outside diameter of 0.6 mm or more. In making larger reactors 10, 12, head loss or nutrient loss can limit the maximum length of the perfusion membranes 100a if their diameter is very small, whereas gas transfer membranes 100b tend to be usable in long lengths even when small in diameter.

FIG. 1 shows an assembly of hollow fiber membranes, in this example including liquid and gas carrying membranes (i.e. perfusion membranes 100a and gas transfer membranes 100b) woven together perpendicular to each other to create a fabric 14. The woven structure, though optional, provides an even spacing of the hollow fiber membranes 100, some increase in surface area, and provides a stable assembly for handling. Although not relevant to this example, when used in other bioreactors described herein that are potted in a centrifuge, the woven structure also helps keep the hollow fiber membranes 100 in place while a mold is spinning. Optionally, the hollow fiber membranes 100 may be provided in a non-woven form such as in a loose bundle or wrapped around a frame. Wrapping the membranes around a frame produces two layers of membranes in one direction while still providing looped fiber ends, which avoids a need to seal the ends of the fibers when not doing fugitive potting. Two layers of gas transfer membranes may be added to two layers of perfusion membranes by wrapping the gas transfer membranes around a frame orthogonal to the perfusion membranes, inside of, or outside of, the perfusion membranes. A frame can alternatively be wrapped to provide just layers of gas transfer membranes or just two layers of perfusion membranes.

FIG. 1 (like all of the Figures herein) is schematic and not drawn entirely to scale. In particular, the diameter of the hollow fiber membranes 100 and the spacing between them are highly exaggerated. For example, the hollow fiber membranes 100 may have a nominal (i.e. effective) length of 20 cm or more 30 cm or more or 40 cm or more while having an outside diameter of 2 mm or less and a spacing between subsequent parallel membranes of 5 mm or less or 2 mm or less. The weaving pattern shown in FIG. 1 is optional. In alternative weaving patterns, a hollow fiber membrane 100 travelling in one direction may alternatively pass over and under two, three or more perpendicular hollow fiber membranes 100 before crossing to the other side of the perpendicular hollow fiber membranes 100.

Figure 2A:
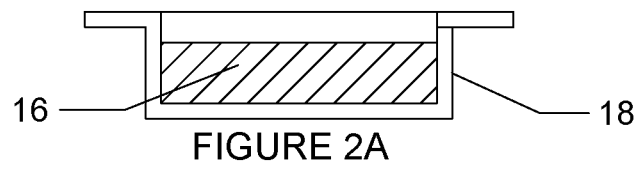
FIGS. 2A, 2B and 2C show a process for potting an assembly of hollow fiber membranes as in FIG. 1 in one part of a cartridge mold.
Figure 2B:
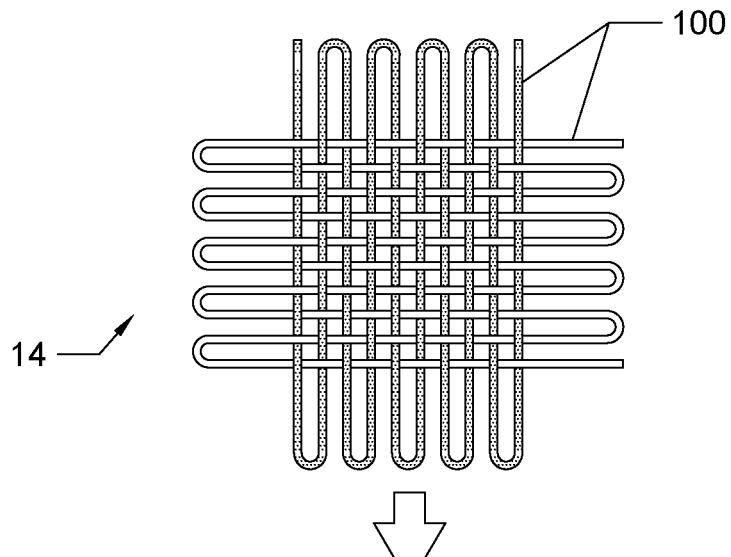
Figure 2C:
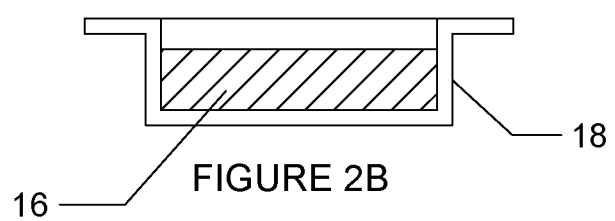
Figure 2C:
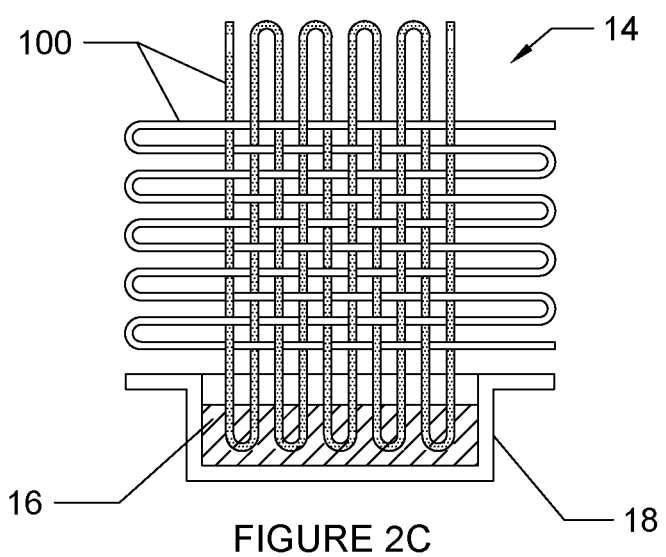

FIGS. 2A, 2B and 2C show a schematic description of a process for potting, or sealing ends, of an assembly of hollow fiber membranes 100, for example fabric 14 as in FIG. 1, with a potting material 16 held in one part of a cartridge mold 18. In this example the potting material 16 is curable liquid epoxy. In other alternatives, another potting material such as a polyurethane resin may be used as the potting material 16. In FIG. 2A, the cartridge mold 18 is filled with potting material 16 in a liquid state. In FIG. 2B, the end loops of the hollow fiber membranes 100 on one side of the fabric 14 are inserted into the liquid potting material 16. In FIG. 2C, the potting material 16 is allowed to cure into a solid. This procedure is repeated for the other three sides of the fabric 14, optionally after taking the solid potting material 16 out of the cartridge mold 18 and/or cutting away parts of the potting material 16 and/or cartridge mold 18. In an optional case wherein the hollow fiber membranes 100 do not have looped ends, the ends of the hollow fiber membranes 100 can be closed before potting by, for example, dipping their ends in a viscous thermosetting resin or wax, heat sealing or welding them shut, or by placing a fugitive material such as a glycerin based gel below the potting material 16 at the bottom of the potting cavity in the cartridge mold 18 such that the ends of the hollow fiber membranes 100 are in the fugitive material. Although only one sheet of fabric 14 is shown to simplify the drawing, multiple layers of fabric 14 stacked together, optionally with spacers between them, or other assemblies of hollow fiber membranes 100 may be potted together in a cartridge mold 18. The solidified potting material 16 can be sealed, for example by an adhesive or gasket, into headers to create an assembly that can be immersed without an associated shell into any container of first liquid media large enough to hold the assembly. Alternatively, the solidified potting material can be sealed into an associated shell configured to contain first liquid media.

Figure 3A:
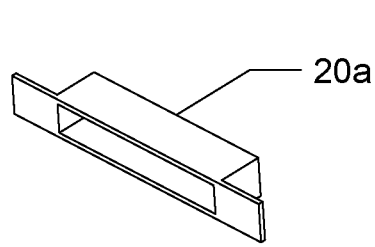
FIGS. 3A and 3B are isometric views of, respectively, a first part of another cartridge mold and second part of another cartridge mold.
Figure 3B:
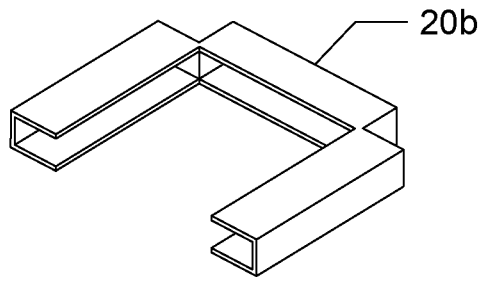
Figure 3C:
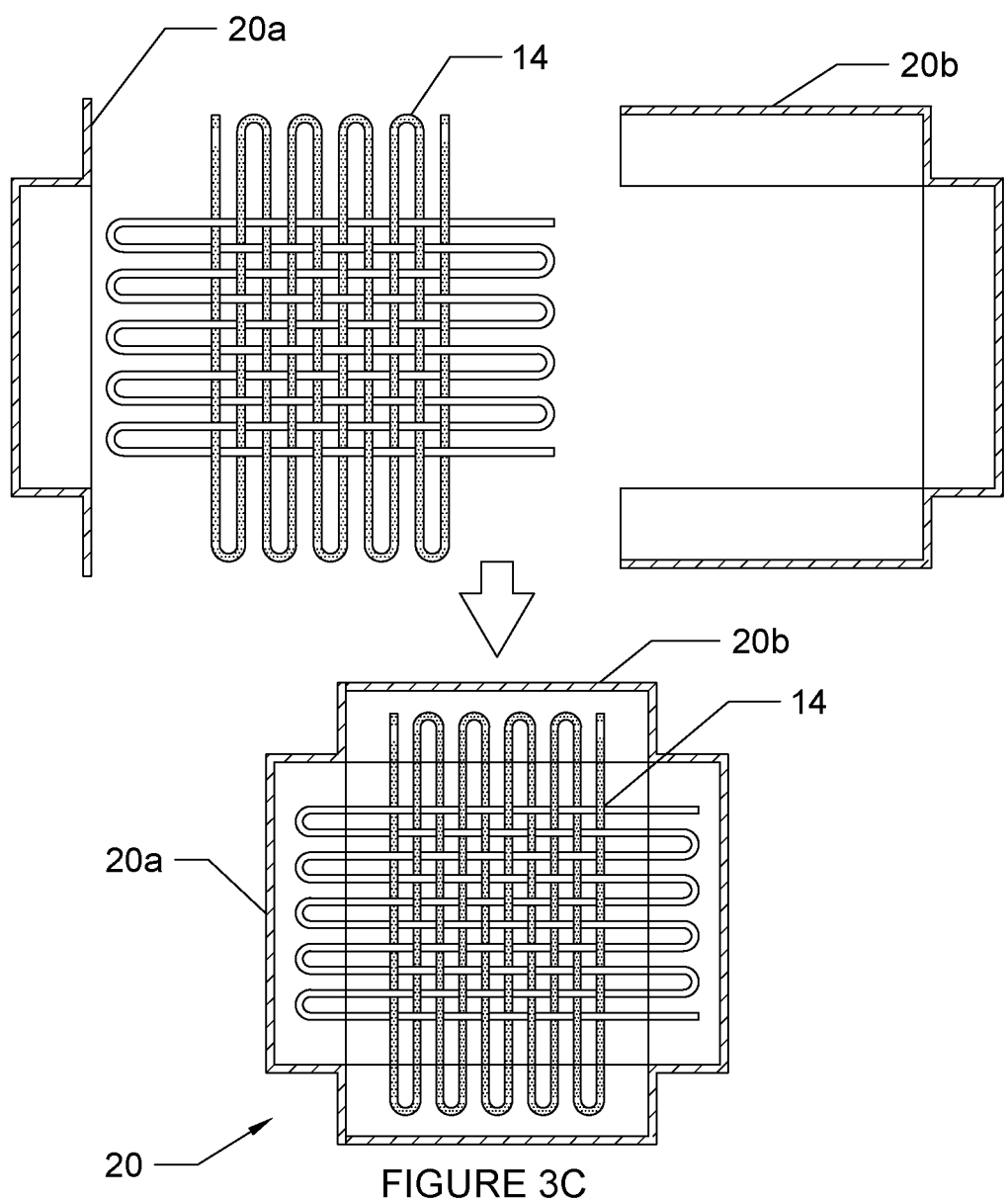
FIG. 3C shows some steps in a process for potting the assembly of hollow fiber membranes of FIG. 1 in the cartridge mold of FIGS. 3A and 3B.

Referring to FIGS. 3A, 3B and 3C, a second cartridge mold 20 is made up of multiple parts that assemble to form a frame. In the example shown, a first part 20a and a second part 20b, shown in FIGS. 3A and 3B respectively, together enclose all four sides of an assembly of hollow fiber membranes 100 such as fabric 14. As shown in FIG. 3C, the second cartridge mold 20 is created by inserting fabric 14 into the second part 20b and then attaching, for example by an adhesive or plastic welding, the first part 20a to the second part 20b. The hollow fiber membranes 100 may then be potted into the resulting second cartridge mold 20 generally as described in FIG. 1 except that the potting material 16 is injected or poured into each of the four sections of the second cartridge mold 18 in turn, while that section is pointing downwards, after the hollow fiber membranes 100 have been placed in the cartridge mold 20. Alternatively, potting material 16 may be injected into all four sections of the second cartridge mold while rotating the second cartridge mold 20 to provide centrifugal potting. Although only one sheet of fabric 14 is shown to simplify the drawing, multiple layers of fabric 14 stacked together, optionally separated by spacers, or other assemblies of hollow fiber membranes 100 may be potted together in a second cartridge mold 20.

Figure 4:
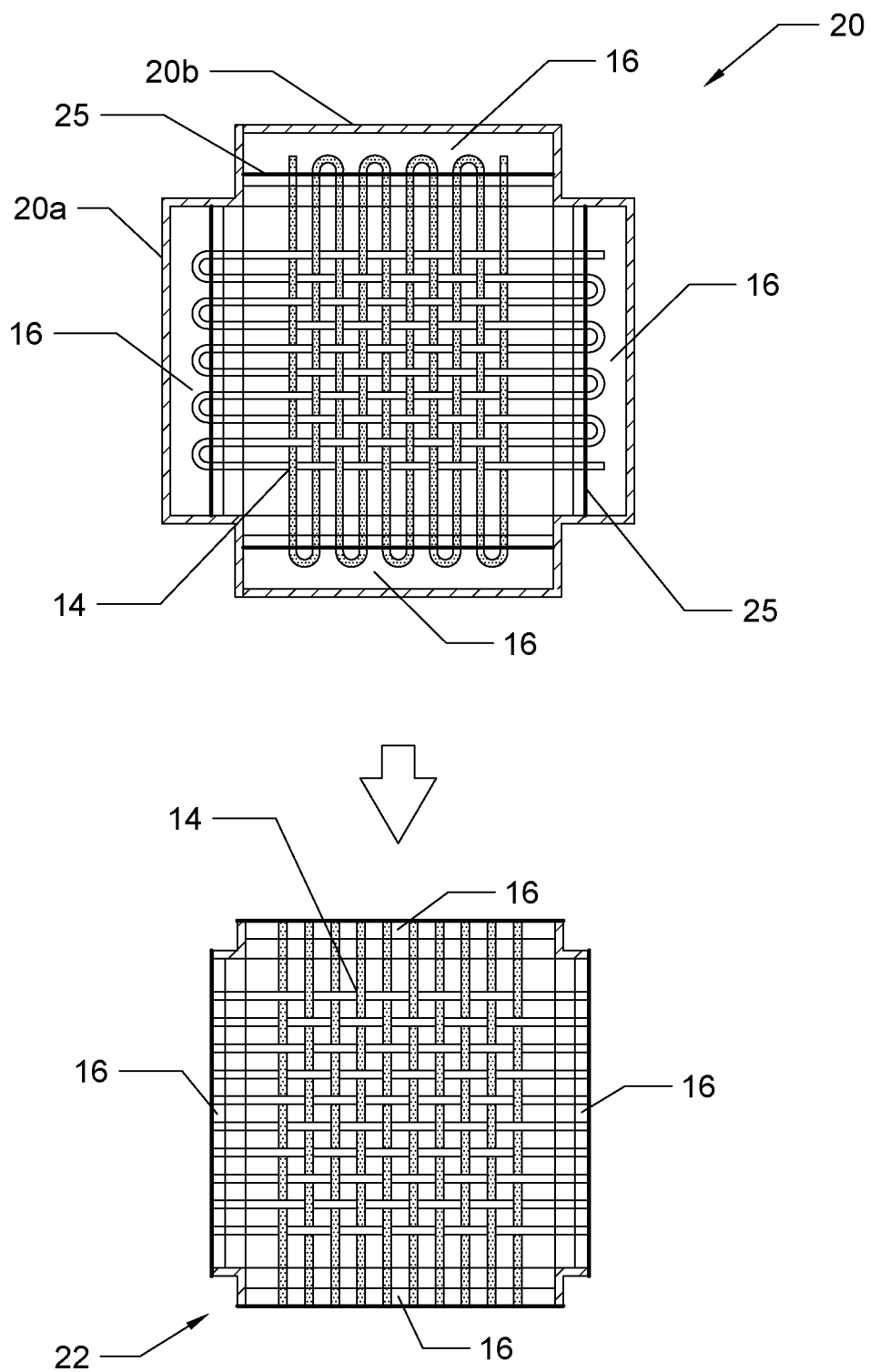
FIG. 4 shows a further step in a process for potting as in FIG. 3C and a step of removing parts of the cartridge mold and potting material to provide a cartridge.

FIG. 4 is a schematic view of a step of removing (i.e. cutting away) parts of the second cartridge mold 20 along cut lines 25, after potting the hollow fiber membranes into potting material 16 that has solidified, to provide a membrane cartridge 22. Open ends of the hollow fiber membranes 100 are exposed through the hardened potting material 16 between remaining parts of the second cartridge mold 20 at the sides of the cartridge 22. Alternatively, if the ends of the hollow fiber membranes were sealed in a fugitive material, the fugitive material may be removed from the ends of the hollow fiber membranes 100, for example through a hole drilled in the second cartridge mold 20 or by cutting through the second cartridge mold 20, with or without cutting through the hollow fiber membranes 100 depending on whether the ends of the hollow fiber membranes 100 were looped or otherwise sealed before being inserted into the fugitive material or not.

In the example shown, pieces of the second cartridge mold 20 remain attached to the potting material 16. In other alternatives, these remaining pieces of the second cartridge mold 20 are separated from the potting material 16. The cutting step shown in FIG. 4 can be similarly applied to a cartridge made using the cartridge mold 18 of FIG. 2C.

Figure 5:
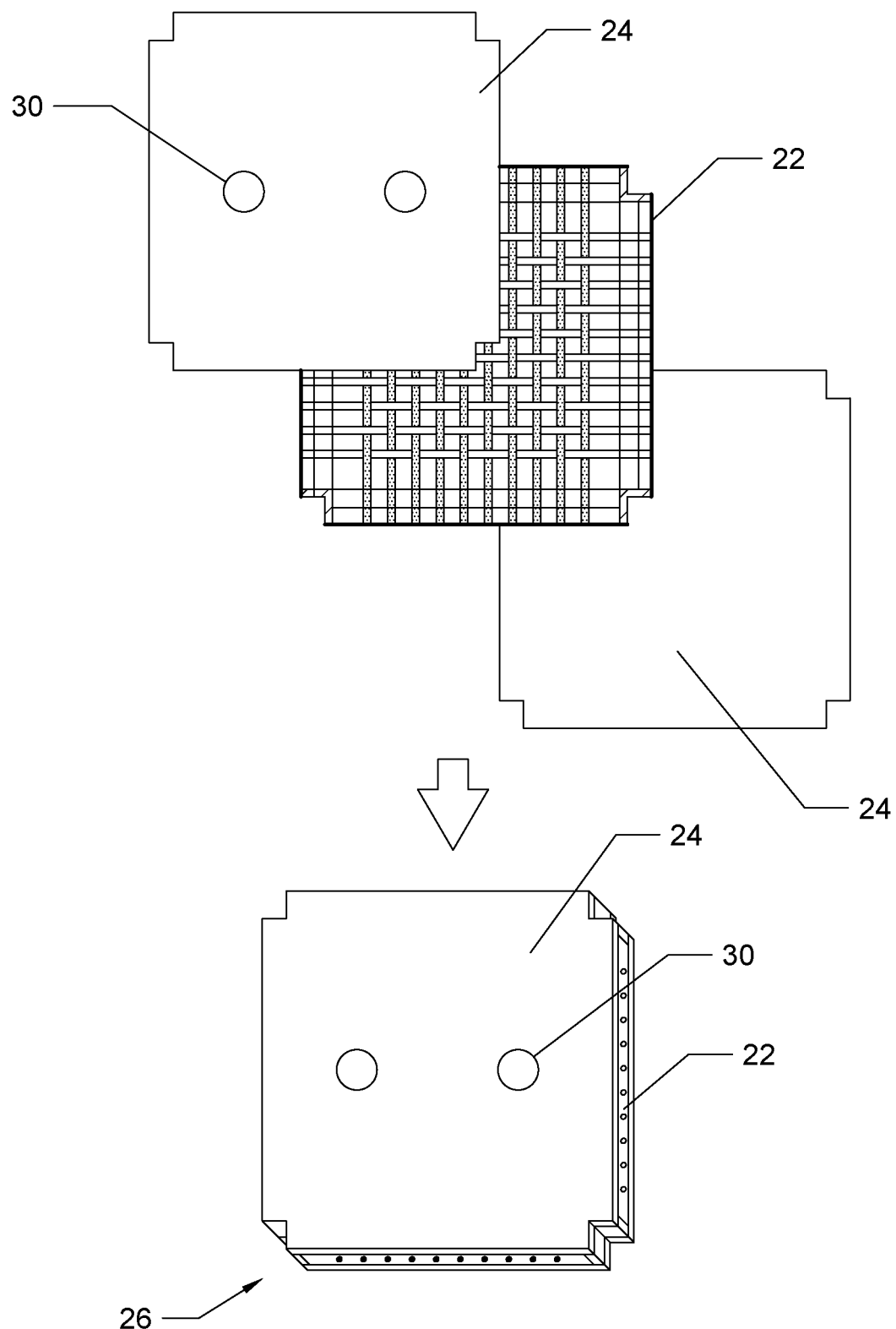
FIG. 5 shows steps in a process of producing an intermediate assembly using a cartridge as in FIG. 4.

FIG. 5 shows some initial steps in a process of forming a single cartridge reactor 10 as shown in FIG. 7. Upper and lower impermeable pieces, in this case pieces of flexible plastic film 24 or a plastic sheet, optionally with ports 30 that can be used for cell harvesting or other purposes, are attached to the remaining parts of the cartridge 22. For example, the films 24 may be glued to the potting material 16 or remaining pieces of the second mold 20 of the cartridge 22. Optionally, the impermeable pieces may be rigid sheets of plastic instead of films 24. Optionally, the impermeable pieces may be translucent or transparent. The resulting intermediate assembly 26 is shown on the bottom of FIG. 5.

FIG. 6A is a schematic view of further steps in a process of forming a single cartridge bioreactor 10 (shown in FIGS. 7A and 7B) in which a fluid connector 28, is attached, for example glued, over an edge of the intermediate assembly 26. A fluid connector 28 (alternatively called a header or manifold) which may be a liquid supply connector, a liquid exhaust connector, a gas supply connector or a gas exhaust connector. FIGS. 6B and 6C show further details of the fluid connector 28. Four generally similar fluid connectors 28 may be used to enclose all four edges of the intermediate assembly 26.

Figure 7A:
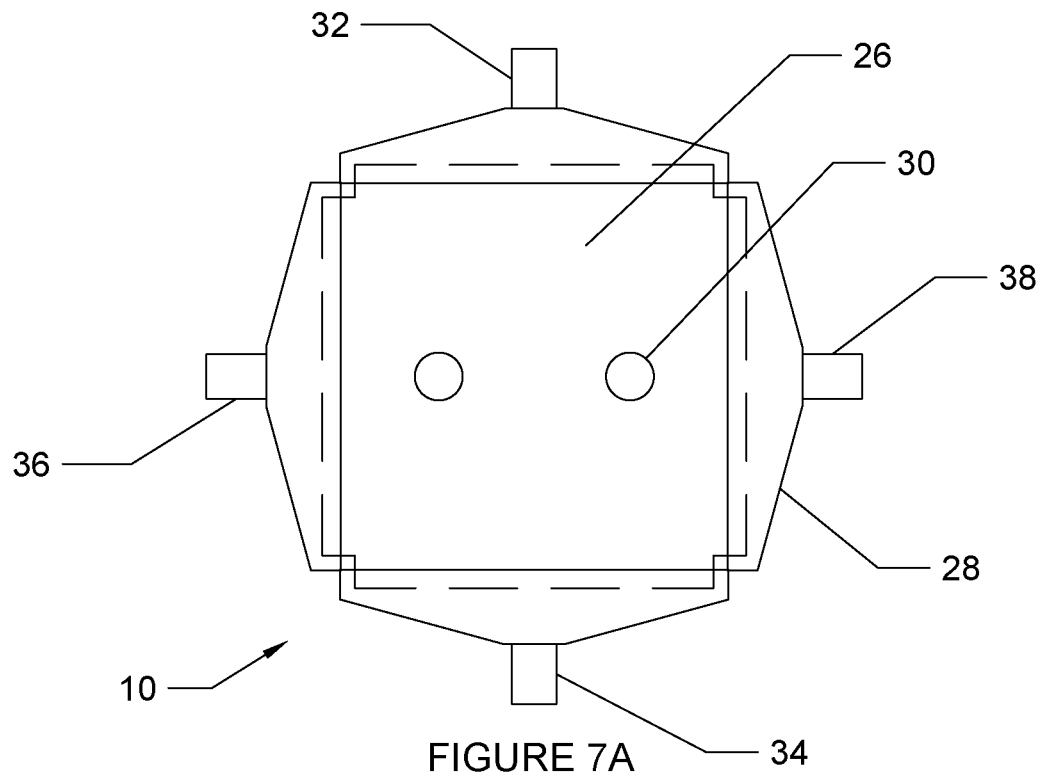
FIG. 7A is a top view of a single cartridge reactor.
Figure 7B:
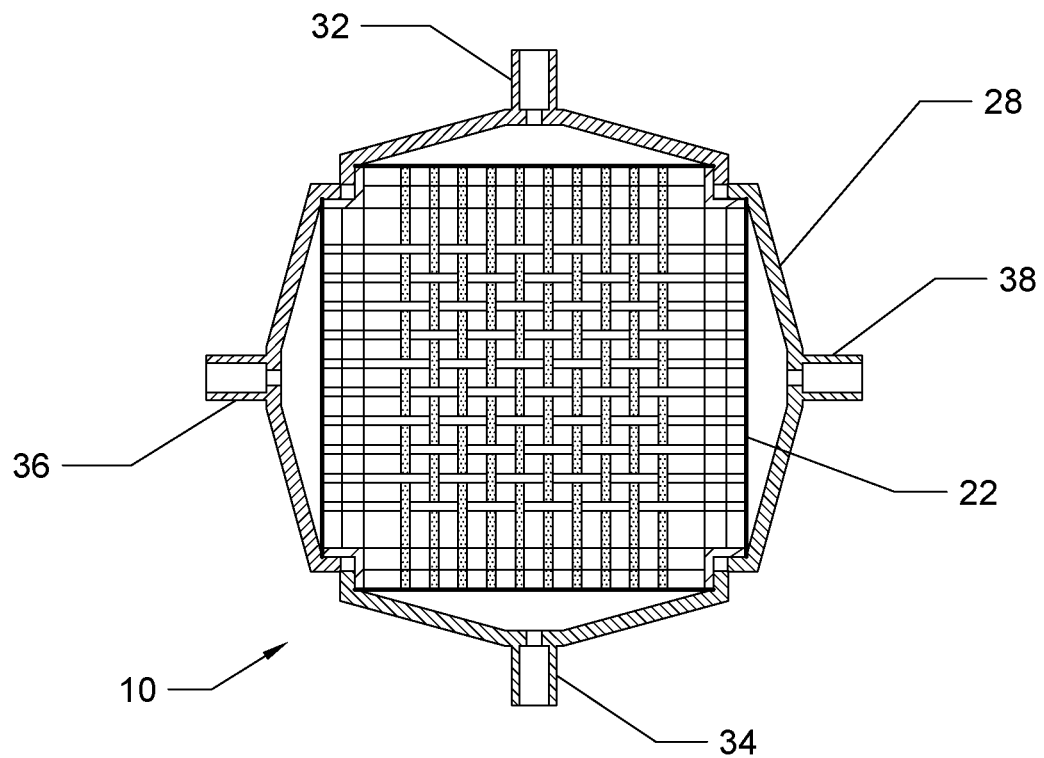
FIG. 7B is a cross section of the single cartridge reactor of FIG. 7B.

FIGS. 7A and 7B are schematic top and top cross-section views of a single cartridge reactor 10 respectively. The single cartridge reactor 10 was produced by continuing the process shown in FIG. 6A to seal four fluid connectors 28 to the four edges of the intermediate assembly 26. The single cartridge reactor 10 has a gas inlet 32 and a gas outlet 34 in communication with gas transfer membranes 100b inside of the single cartridge reactor 10. The single cartridge reactor 10 has a liquid inlet 32 and a liquid outlet 34 in communication with perfusion membranes 100a inside of the single cartridge reactor 10. The perfusion membranes 100a may thereby be used for nutrient diffusion and/or waste or harvested product removal by way of a second liquid media carried by the perfusion membranes 100a. There may be more or less ports 30 than in the example shown. Ports 30 may be used, for example as cell harvesting ports, for sensors, for sampling ports or septums, or to add or remove first liquid medium or headspace gasses.

As shown in FIGS. 7A and 7B, the single cartridge reactor 10 defines a plenum that holds first liquid media around the outside of the hollow fibers 100. Alternatively, a single cartridge reactor can be made in a similar way but by attaching fluid connectors 28 to a cartridge 22 instead of intermediate assembly 26. This alternative single cartridge reactor does not define a plenum itself but can be immersed in first liquid media held in any container large enough to hold the alternative single cartridge reactor. The container may be a sealed container or an open tank. The first liquid media may completely fill the container or there may be a free surface of the liquid media above the alternative single cartridge reactor.

Figure 8B:
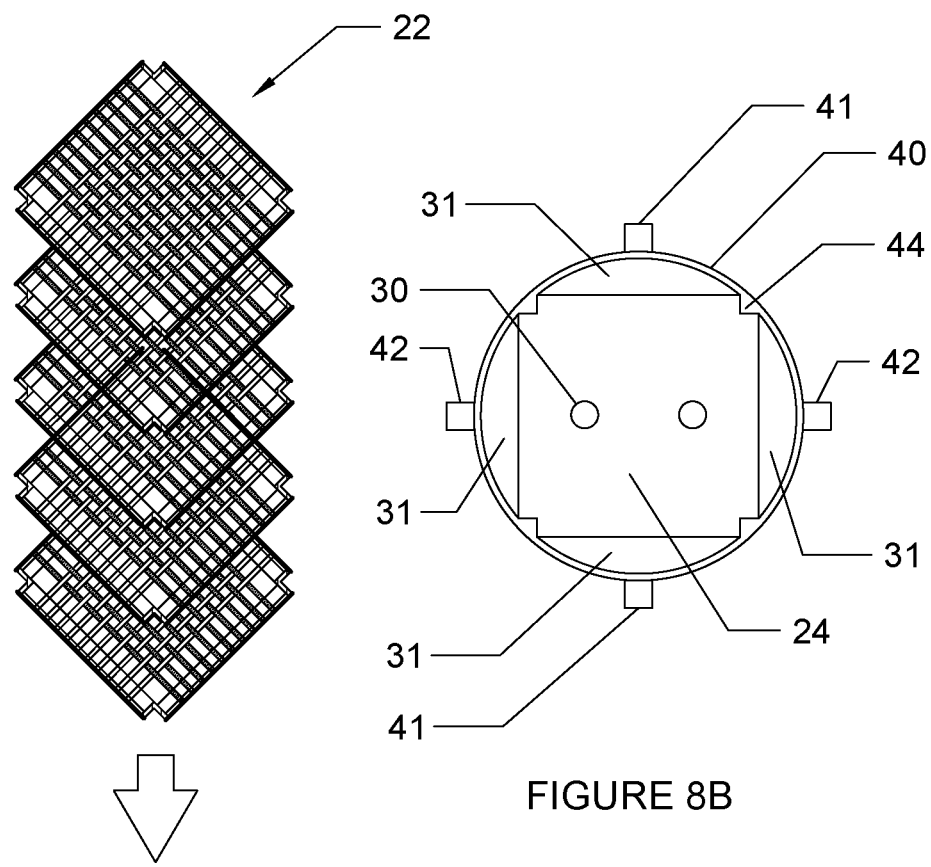
FIG. 8B is a top view of the multi-cartridge reactor.
Figure 8A:
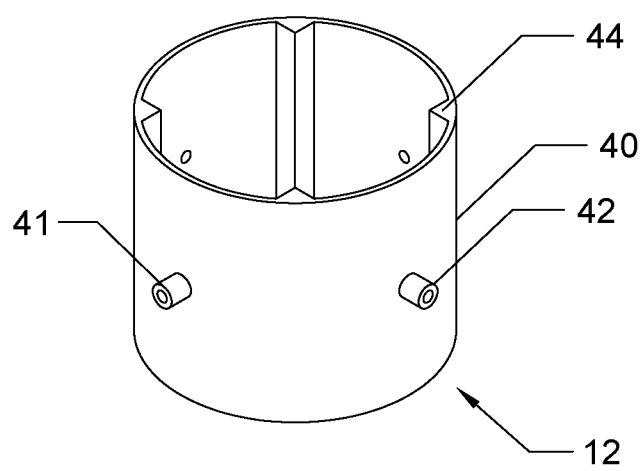
FIG. 8A shows some steps in a process of making a multi-cartridge reactor.

FIG. 8A is a schematic isometric view of a multi-cartridge reactor 12 being assembled. FIG. 8B shows a top view of the multi-cartridge reactor 12. In the multi-cartridge reactor 12, two or more of the cartridges 22 described above, or optionally intermediate assemblies 26, are stacked, optionally with intervening glue or gasket layers to seal them together. The stacked cartridges 22 (or optionally intermediate assemblies 26) are loaded into a shell 40. A cartridge 22 at the bottom of the stack has a film 24 on its lower side. Alternatively, the potting material 16 or remaining parts of second cartridge mold 20 can be sealed, for example by an adhesive or gasket, to a floor of the shell 40, which may be integral with the shell 40 or provided by a cap (not shown). Similarly, a cartridge 22 at the top of the stack has a film 24 on its upper side, as shown in FIG. 8B. Alternatively, the potting material 16 or remaining parts of second cartridge mold 20 can be sealed, for example by an adhesive or gasket, to a top of the shell 40, which may be integral with the shell 40 or provided by a cap (not shown).

In the example of FIG. 8B, a lower cartridge 22 is sealed directly to an integral floor of the shell 40. An upper cartridge 22 has a film 24 on its upper side with ports 30. Fillers 31 between the outer periphery of the upper cartridge 22 and the inner periphery of the shell 40. Spaces between the inside of the walls and floor of the shell 40, the fillers 31 and the edges of the cartridges 22 or intermediate assemblies 26 function as fluid headers or manifolds communicating between ports 41 or 42 in the shell 40 and the open ends of the hollow fiber membranes 100 exposed through the cut lines 25 at the edges of the cartridges 22 or intermediate assemblies 26. Corners of the cartridges 22 or intermediate assemblies 26 are sealed to the inside of the shell 40, for example at abutments 44, for example by an adhesive. Gas ports 41 are provided on opposite sides of the shell 40 to provide an inlet and outlet for air in communication with the gas transfer membranes 100b. Liquid ports 42 are provided on opposite sides of the shell 40 to provide an inlet and outlet for liquid in communication with the perfusion membranes 100a. The ports 30 allow first liquid media and/or gasses to be remove from the extra membrane space. Optionally other ports, whether provided in a film 24 or an end cap sealed to an upper or lower cartridge 22, can be used to provide one or more of for example a viewing port, a cell harvesting port, a bubble aerator for detaching cells or mixing in communication with the extra-membrane space, or one or more sensors. Optionally, ports at opposite ends of the shell 40 can be used to provide a sweeping flow of a fluid through the multi-cartridge reactor 12 for example to aid in cell harvesting, to provide mixing or renewal of first liquid media, to dislodge gas bubbles formed within the multi-cartridge reactor 12 by cellular respiration, to inhibit settling of cells or to redistribute cells that have settled.

The multi-cartridge reactor 12 can be made larger by using a longer shell 40 and stacking more cartridges 22 or intermediate assemblies 26 into it. The plenum inside of the shell 40 may be, for example, 50% or more, 100% or more or 200% or more of the length of the hollow fiber membranes 100, for example the perfusion membranes 100a. The interior volume (i.e. the extra-capillary space) of the multi-cartridge reactor 12 can thereby be increased without increasing the length of hollow fiber membranes 100. This may help reduce head losses in the membranes or avoid providing an uneven or deficient distribution of one or more nutrients, including a gas such as oxygen. Alternatively or additionally, the shell 40 may be rectangular and configured to hold rectangular cartridges 22 or intermediate assemblies 26. Rectangular cartridges 22 or intermediate assemblies 26 may have, for example, gas transfer membranes 100b that are longer than perfusion membranes 100a.

Although the cartridge 22 shown in FIGS. 1-8 is generally square, cartridges of other shapes can also be made. For example, a rectangular cartridge can be made. A rectangular fabric 14 is made, optionally, with the gas transfer membranes 100b longer than the perfusion membranes 100a. In the example of FIG. 2, relatively longer and shorter cartridge molds 18 are made for the longer and shorter sides of the fabric 14. In the example of FIGS. 3A and 3B, the second cartridge mold 20a and the middle portion of the second cartridge mold 20b are made longer than the end portions of second cartridge mold 26b, according to the dimensions of the rectangular fabric 14.

Figure 11:
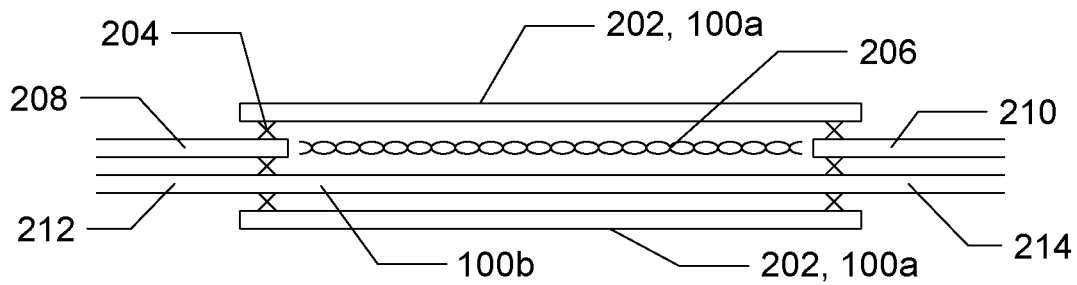
FIGS. 11 and 12 are cross-section and top views respectively of a sheet form membrane cartridge that may be used, for example, to grow tissues or individual cells.
Figure 12:
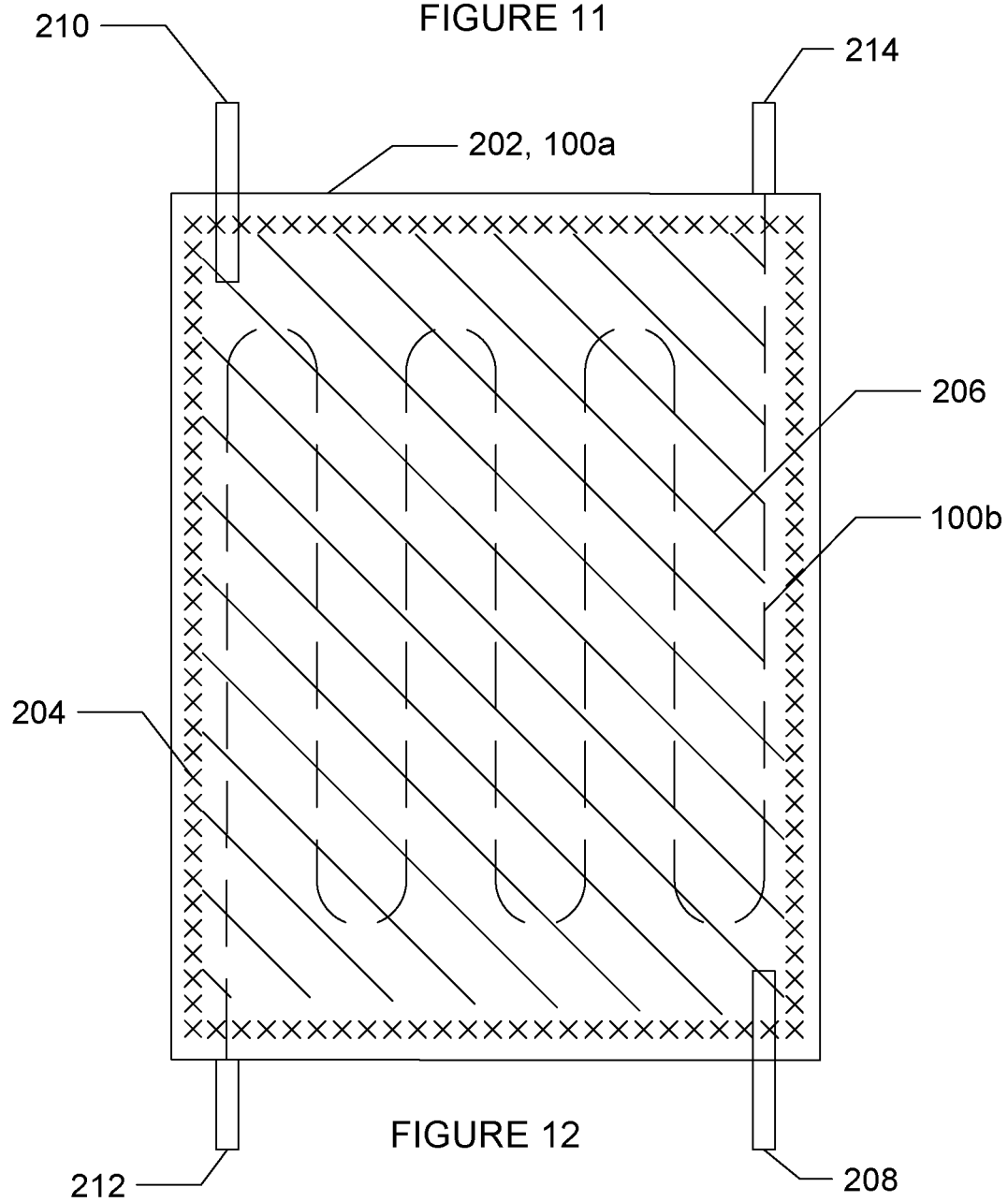

The format of FIGS. 1 to 8 may alternatively be used to prepare a bioreactor with one or more flat sheet membrane assemblies by substituting the structure of FIGS. 11 and 12 or 13, or another structure with flat sheet membranes described herein, for the cartridges 22 or intermediate assemblies 26. In a single cartridge reactor, equivalents or analogs of the fluid connectors 28 are made to join to one or more entire the edges of the flat sheet membranes or only to the ports of the flat sheet membrane assemblies. In a multi-cartridge reactor, gaps are left around and between the flat sheet membranes so that the first liquid media can circulate through the reactor. Appropriate tubes or other structures can be added to connect to the ports of the flat sheet membrane assemblies.

In another alternative, a single cartridge reactor 10 as in FIG. 7 can be made with fluid connectors 28 having ports in the upper and lower surfaces of the fluid connectors 28. In this way, when a stack of single cartridge reactors, with or without the films 24 or other impermeable pieces, is formed the fluid connectors 28 are connected by the ports and form manifolds perpendicular to the hollow fiber membranes 100. Optionally, the upper and lower surfaces of the fluid connectors 28 can be glued together to form a vessel that defines the outside of the extra-membrane space. Alternatively, the assembly can be immersed in a separated vessel. By either method, an alternative multi-cartridge reactor can then be made without using a specially formed shell such as shell 40.

Figure 9:
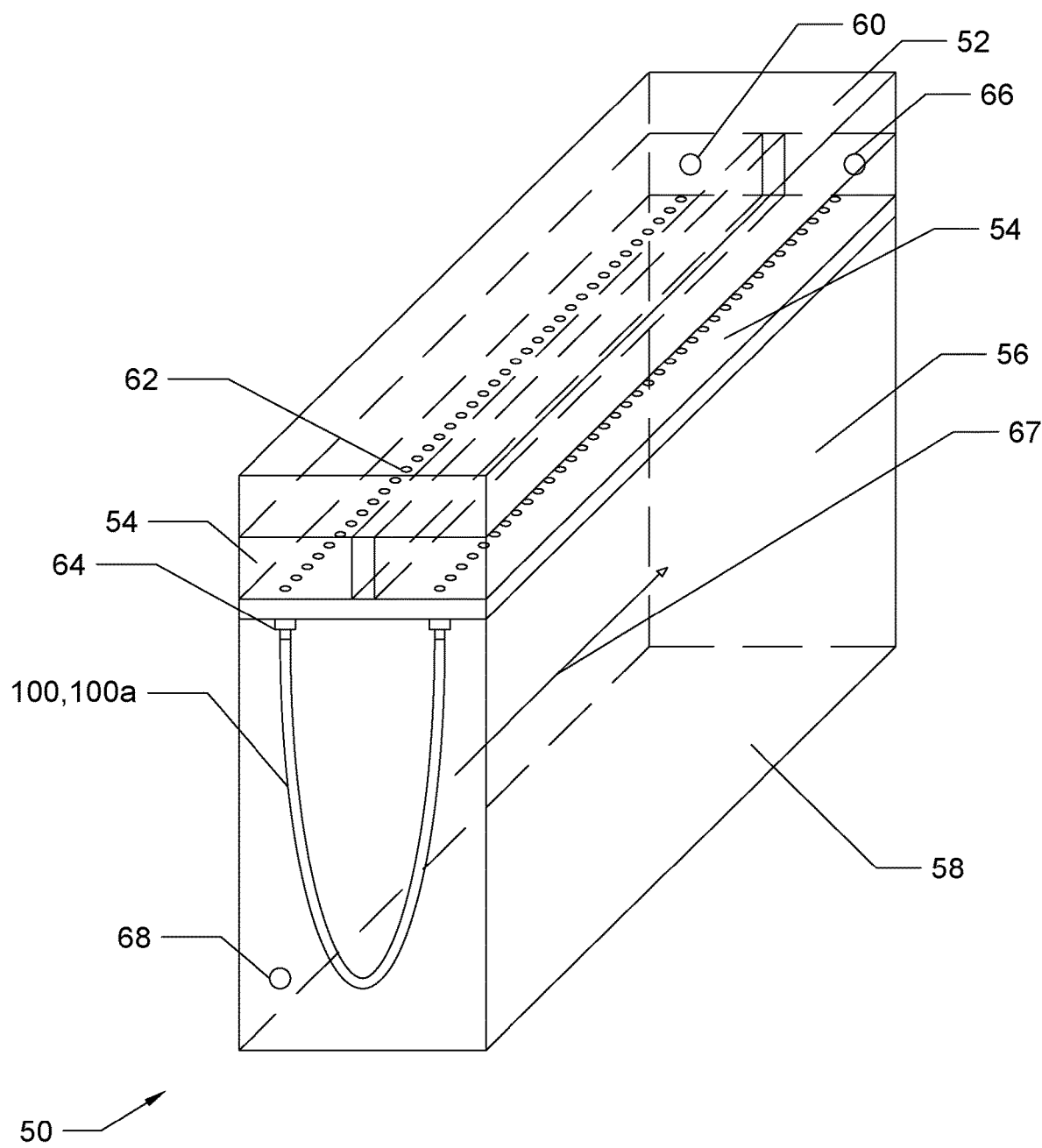
FIG. 9 is an isometric view of another cell culture bioreactor.

FIG. 9 shows another cell culture bioreactor 50. Hollow fiber membranes 100 are provided in the form of loops. Optionally, the bioreactor 50 may be inverted such that the loops extend upwards. With sufficient packing density (FIG. 9 shows much fewer hollow fiber membranes 100 than are actually used), or a mild upwards flow of the first liquid media, the loops do not fall if extending upwards. In the example shown, the form (i.e. plan view shape) of the bioreactor 50 is rectangular. Optionally, the form of the bioreactor 50 may be square or cylindrical. However, the rectangular form can provide a configuration with material length perpendicular to the hollow fiber membranes 100, which allows for larger structures to be provided without increasing the length of the hollow fiber membranes 100. This may help reduce issues of nutrient transport near the downstream end of the fibers, head loss in the fibers, or variable conditions within the bioreactor 50. For example, the bioreactor may be at least 50% as long as, 100% as long as, or 200% as long as the hollow fiber membranes 100, wherein length of the bioreactor is measured perpendicular to the fibers. Similarly, a bioreactor as in FIG. 8 may be at least 50% as long as, 100% as long as, or 200% as long as the hollow fiber membranes 100, wherein length of the bioreactor is measured perpendicular to the hollow fiber membranes 100.

The bioreactor 50 of FIG. 9 is divided vertically into an electronics and/or sensor housing 52, hollow fiber internal flow chambers 54, a hollow fiber external flow chamber 56 and a cell collection area 58. An internal fluid (i.e. a first or second nutrient media) enters the bioreactor 50 through an internal fluid feed inlet port, then flows through one of the hollow fiber internal flow chambers 54 to a several hollow fiber inlet ports 62. Each hollow fiber inlet port 62 is in fluid communication with a hollow fiber connector 64 (for example a plug of a potting material), which is in turn connected to one or more hollow fiber membranes 100, for example perfusion membranes 100a. The internal fluid passes through the lumens of the hollow fiber membranes 100 into another one of the hollow fiber internal flow chambers 54, which is connected to an internal fluid outlet port 66. External fluids (which may be a gas), if any, can be supplied through an external fluid feed port 68 and removed through another port (not visible) on the back of the bioreactor 50. The length 67 of the bioreactor 50 is perpendicular to the hollow fiber membranes 100. The bioreactor 50 may be disposable or reusable, as may be any of the other reactors or bioreactors described herein. Straight hollow fiber membranes 100 may be used instead of curved hollow fiber membranes 100, for example by moving one of the hollow fiber internal flow chambers 54 to the bottom of the bioreactor 50.

Figure 10:
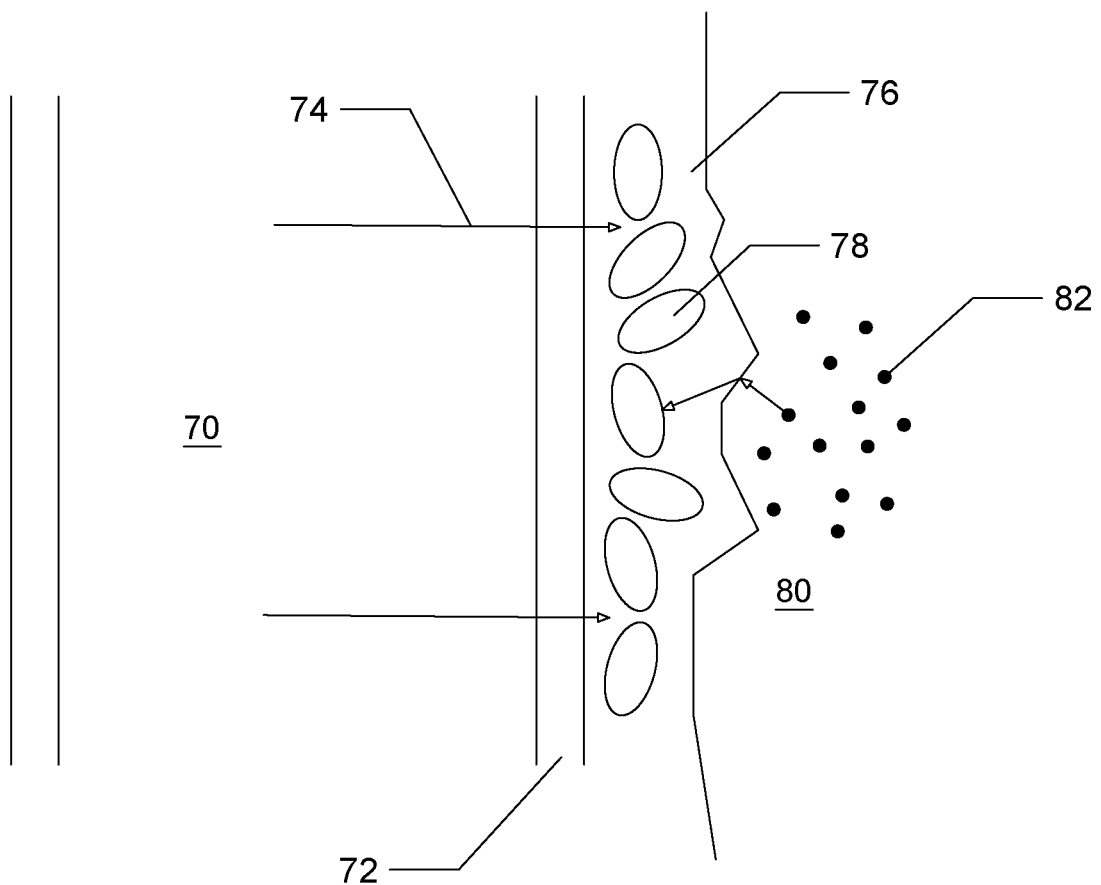
FIG. 10 is a schematic view of a membrane in the cell culture bioreactor of FIG. 9 supporting cells within a liquid film.

The extra-membrane space may be filled with liquid. Alternatively, for example as shown in FIG. 10, the extra-membrane space may be primarily filled with a gas such as air. A nutrient liquid, which may be first liquid media supplied directly to the outside of the fibers and/or second liquid media supplied through the hollow fiber membranes 100, is provided in a film around the cells, which are attached to the outsides of the membranes. The cells are located primarily within a liquid film. A liquid or gas flows past (i.e. within) the membrane on the side opposite the cells, and oxygen (and/or other gasses) or dissolved or dispersed nutrients flow to the cells through the membrane. Although shown as used with the bioreactor of FIG. 9, this mode of operation may be used with any bioreactor described herein. Gas transfer membranes are generally not required with the mode of operation of FIG. 10 but can be optionally used to increase the supply or removal of a gas.

As applied to any bioreactor described herein, FIG. 10 shows the use of a gas phase external fluid 80 in the extra-membrane space, which may be used to provide oxygen mass transfer to the cells 78. Oxygen is only slightly soluble in water, which can create a barrier for cell growth. In FIG. 10, an internal fluid 70 inside of a membrane 72 provides a source for nutrients 74 and optionally bulk fluid to feed a liquid film 76 on the outside of the membrane 72. Cells 78 grow in the liquid film 76. External fluid 80, for example air, containing oxygen 82, is in contact with the outside of the liquid film 76. Growing the cells 78 within the liquid film 76 provides a very small distance between the oxygen 82 and the cells 78 to provide for a high oxygen transfer rate. Optionally, a two-film and/or penetration theory may be used.

FIGS. 11 and 12 show a flat membrane assembly 200 including a flat sheet membrane 202. The word "flat sheet" is used for consistency with the term used in membrane filtration but the sheet can be curved. The sheet form of this assembly provides a support suitable for growing cell tissues. However, the flat membrane assembly 200 can also be used to grow cells that are not in a tissue. The flat sheet membrane assembly 200 can be immersed in first liquid media in a vessel Two flat sheet membranes 202 are attached together (for example with an adhesive 204 or by welding) along their edges to form a sealed inner volume. Alternatively, one flat sheet membrane 202 may be folded over and sealed along its un-folded edges to form a sealed inner volume. A separation layer of the membranes 202 may be located on either the inside or the outside of the flat sheet membrane assembly 200. Optionally, the flat sheet membrane 202 is made by coating a substrate with a responsive material, for example by coating a fiberglass paper with an oxazoline or coating cellulose paper with POEGMA. Optionally, a spacer material 206, for example woven feed spacer as used in spiral wound membranes or a 3D spacer may be added to help prevent the inner volume from collapsing and to provide a channel for nutrient fluid flow. Optionally, a rigid spacer (not shown) may also be added to provide a particular shape, for example flat or curved, to the assembly. In another option, a gas transfer membrane 100b, or a plurality of gas transfer membranes attached to a header, may be added inside the inner volume to supply oxygen and/or remove carbon dioxide. A nutrient solution may be added to the membrane assembly 200 by way of a nutrient inlet 208 and remove by way of a nutrient outlet 210. A gas such as air or modified air may be added to the gas transfer membrane 100b through a gas inlet 212 and removed through a gas outlet 214. The assembly may be operated in a perfusion culture mode wherein a nutrient solution flows through the inner volume and nutrients diffuse through the flat sheet membranes 202 to a cell tissue growing on the outside of the assembly. Oxygen is transferred through the gas transfer membrane 100b to the nutrient solution and from there to the cells. Although the gas transfer is less direct than in some of the other bioreactors, the distance between the outer surface of the gas transfer membrane 100b and the cells is still very low, for example 10 mm or less or 5 mm or less.

Alternatively, the gas transfer membranes 100b is omitted. In some examples the flat sheet membrane 202 is itself a gas transfer membrane. Flat sheet gas transfer membranes can be made, for example, by coating a woven or non-woven fabric with PDMS or another silicone. In other examples, the flat sheet membrane 202 provides only a perfusion membrane. When alternated in a bioreactor, these membranes assemblies provide spaces between them that are supplied with both gaseous and aqueous nutrients.

The flat membrane assembly 200 may be immersed in a bioreactor such that a cell culture media is provided in bulk or in a film on the outside of the assembly.

Figure 13A:
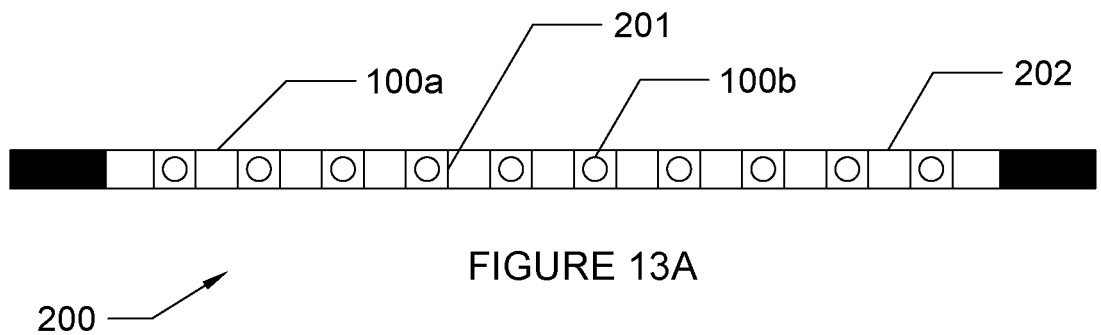
FIGS. 13A and 13B are schematic side and top cross-sectional views of another sheet form membrane cartridge.
Figure 13B:
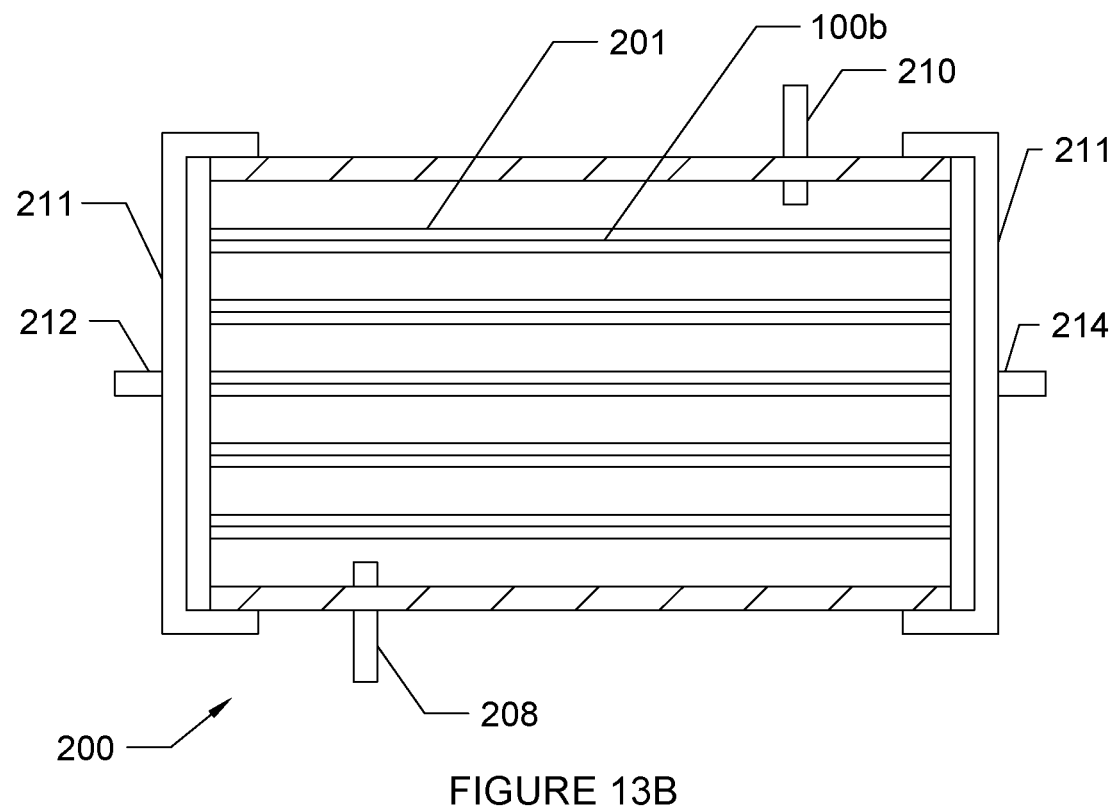

FIGS. 13A and 13B show an example of another flat membrane assembly 200 made using a 3D spacer 201. The 3D spacer 201 can have flat sheet membranes 202 bonded to it. Alternatively, a flat sheet membrane is provided by way of coating a membrane and/or responsive material directly onto both sides of a 3-D spacer 210 woven supporting structure in the manner used to make an integrated permeate channel filtration membrane. Integrated permeate channel membranes are described, for example, in U.S. Pat. Nos. 7,862,718 and 8,393,477 and International Publication Number WO 2008/141935 A1, which are incorporated by reference. Optionally, the membrane may include a responsive material or have a responsive material attached to it. Hollow fiber gas transfer membranes 100b can optionally be placed through gaps in the 3-D woven spacer.

3D spacers 201 are commercially available for use, for example, in automotive interiors, the shoes or other athletic apparel or composite (i.e. fiberglass or carbon fiber) structures. 3D spacers are available in thermoplastic polymers or fiberglass. A 3D spacer 201 typically has an upper and lower fabric surface separated by filaments that cross from the upper fabric to the lower fabric. The upper and lower fabric surfaces can have membrane materials cast directly on them or can be used to support a separate flat sheet membrane 202. Optionally, a fiberglass 3D spacer 201 can be coated directly with an oxazoline. The crossing filaments do not fill the interior volume of a 3D spacer and so a liquid medium can pass in any direction through the interior volume. The crossing filaments have an orderly arrangement that typically includes clear parallel passages in at least one direction. Gas transfer membranes 100b are optionally placed through these passages. The 3D spacer 201 is dipped in potting material or membrane material on its edges to seal the interior volume. Ports 210 or headers 211 are added to access the gas transfer membranes 100b and the liquid medium carrying space around them. A 3D spacer 201 is typically reasonably stiff and can provide a self-supporting structure.

Figure 14A:
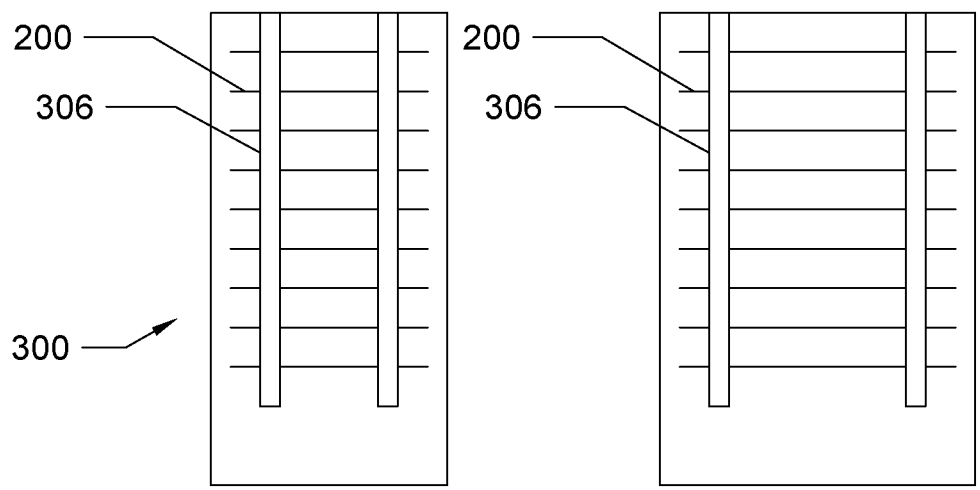
FIGS. 14A, 14B and 14C each show side and front cross-sectional views of alternative bioreactors.
Figure 14B:
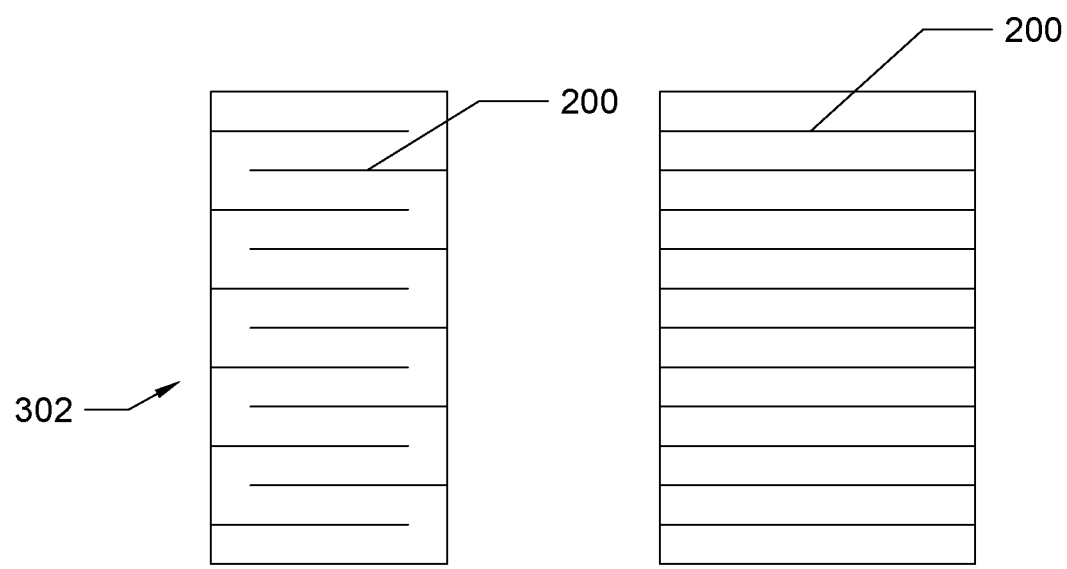
Figure 14C:
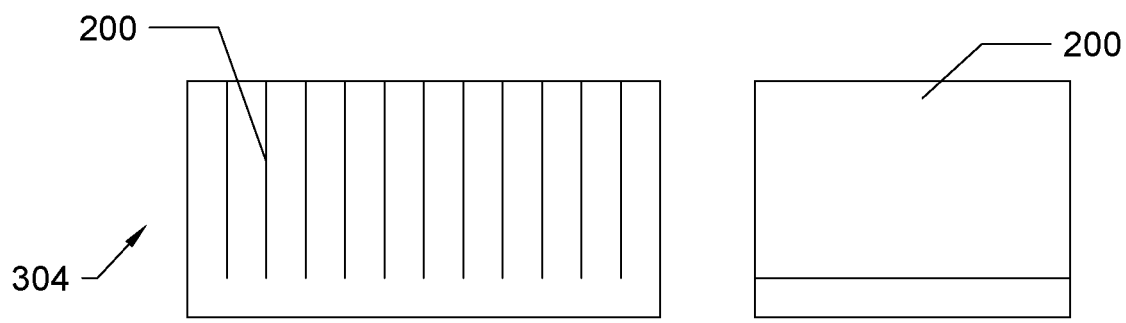

FIGS. 14A, 14B, 14C show other reactor 210 configurations that can be used for flat membrane assemblies 200, or alternatively mats 102 or fabrics 14 of hollow fiber membranes as described herein or other flat form membrane structures. In FIG. 14A, the reactor has four tubes 220. Two tubes 220 are connected to the gas inlet and gas outlet of the flat sheet membrane assemblies 200. Two tubes 220 are connected to the liquid inlet and liquid outlet of the flat sheet membrane assemblies 200. The tubes 220 also optionally hold the flat sheet membrane assemblies 200 in place. In FIGS. 14B and 14C gas and/or liquid is provided to the flat sheet membrane assemblies through one or more the sides of the reactor 210. In all three examples, the flat sheet membrane assemblies 200 can each contain both gas and liquid in their inner-membrane spaces, or the can contain either gas or liquid in their inner-membrane spaces and be placed in the reactor alternating, i.e. gas then liquid then gas then liquid and so on.

Figure 15:
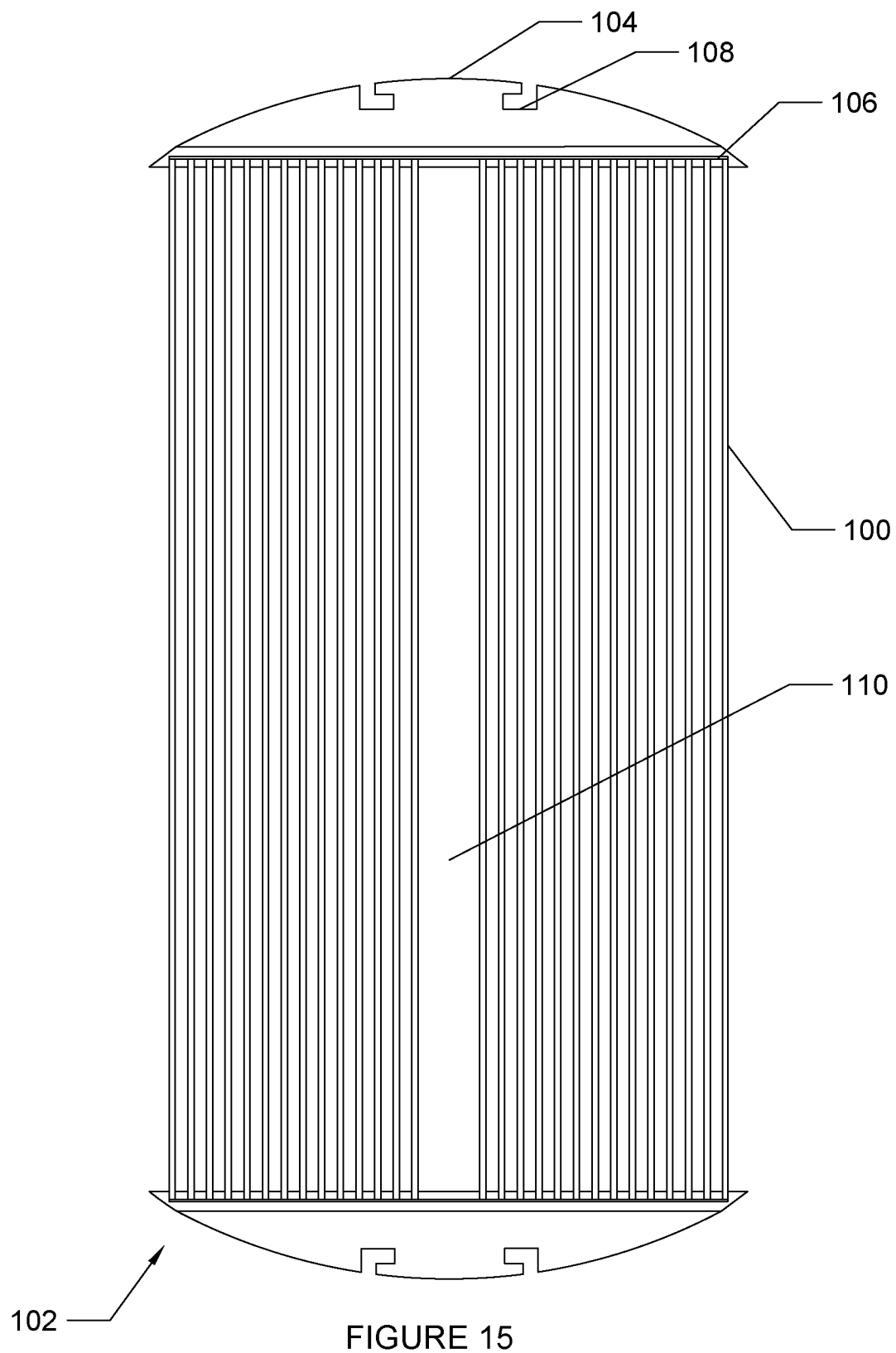
FIG. 15 is a top view of a mat of hollow fiber membranes.

FIG. 15 shows a set of hollow fiber membranes 100. The Figure is not drawn to scale. In particular, the hollow fiber membranes 100 have been shown with an enlarged diameter and reduced number to show that individual hollow fiber membranes 100 are optionally spaced apart from each other by a consistent spacing. Optionally, the diameter of the hollow fiber membranes 100 may be in the range of 0.2 to 2.0 mm. Optionally, the nominal length of the hollow fiber membranes 100 may be in the range of 20 cm to 50 cm. The length of the hollow fiber membranes 100 is specified as measured between the insides of potting heads (to be described further below) to thereby give a length that can be used to calculate an active surface area of the hollow fiber membranes 100. The actual length of the hollow fiber membranes 100 can be longer, for example by 2 to 10 cm, to allow for parts of the hollow fiber membranes 100 that are embedded in a potting compound, extend into a header or manifold, or removed later in a module manufacturing process.

The hollow fiber membranes 100 may be perfusion membranes and/or gas transfer membranes. Perfusion membranes may have pores in the range of microfiltration or less (i.e. smaller), for example in the range of microfiltration, ultrafiltration or nanofiltration. The perfusion membranes typically carry a liquid growth medium. The liquid growth medium has one or more nutrients that diffuse or otherwise travel through the perfusion membranes into a space outside of the hollow fiber membranes 100 where cells are grown, optionally called an extra-capillary space. Gas transfer membranes may have a dense wall of an oxygen-permeable material, for example of polymethylpentene (PMP) or a silicone such as PDMS, an asymmetric wall with a dense region, or a porous wall. Gas transfer membranes with a porous wall are typically made of a melt-spun polymer, which may be inherently hydrophobic and/or treated to make it more hydrophobic, to help inhibit wetting of the pores. The gas transfer membranes may be used to transfer oxygen to the extra-capillary space.

The hollow fiber membranes 100 are arranged together to form a mat 102. The mat 102 is a generally flat or planar structure, for example with hollow fiber membranes 100 extending in length between two parallel planes that are, for example, 5 mm or less apart. In the example shown, the hollow fiber membranes 100 are attached at their ends by a bead of an adhesive 106 to a pair of spacers 104. The adhesive 106 may be, for example, hot melt glue. The adhesive 106 adheres the hollow fiber membranes 100 to the spacers 104 and also closes the lumens at the ends of the hollow fiber membranes 100. The spacers 104 may be a formed or milled piece of plastic or other material. The spacer 104 has one or more keys 108 for use in holding the mat into a mold, to be described further below. Optionally, the hollow fiber membranes 100 may be connected together with one or more lines of monofilament or multifilament threads knit or woven through the hollow fiber membranes 100 in a direction perpendicular to the hollow fiber membranes 100. Optionally, the mat 102 contains multiple subsets of hollow fiber membranes 100 separated by one or more channels 110. The channels 110 provide pathways perpendicular to the hollow fiber membranes 100 that can be used, for example, to facilitate mixing or cell harvesting. Connecting threads, if used, can optionally be restricted to a sub-set of the hollow fiber membranes 100 or span one or more channels 110 to also connect multiple sub-sets of hollow fiber membranes 100 together.

Figure 16:
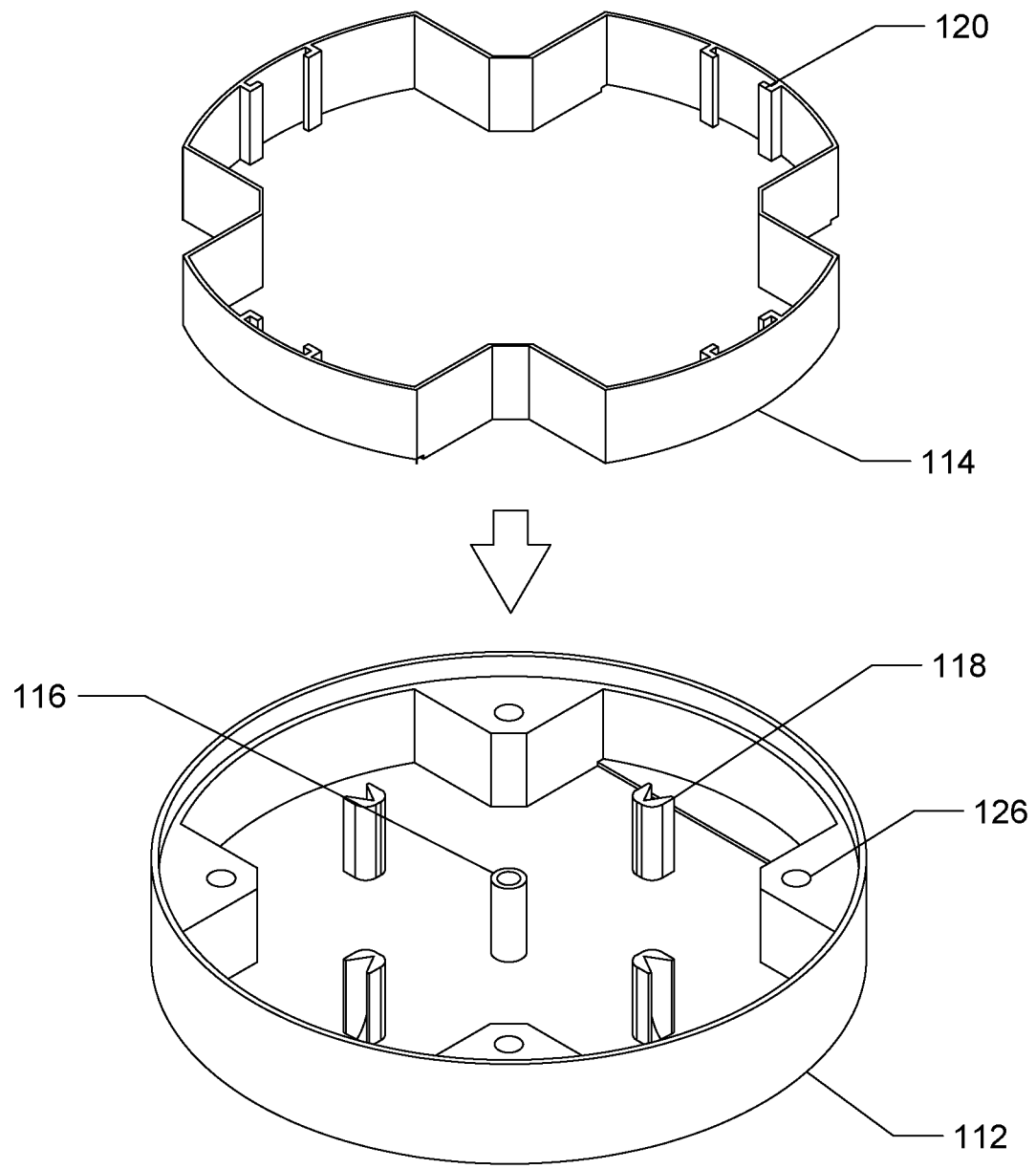
FIG. 16 shows a process of inserting a brace into a mold base.

FIG. 16 shows part of a mold, in particular a mold base 112, and an optional brace 114. The mold base 112 is configured to define the shape of the bottom and sides of one or more potting blocks 142 (see FIG. 19) and/or to support the brace 114 which may form one or more surfaces of a potting block 142. In the example shown, the brace 114 defines three sides (one of which will be later removed) of each of four potting blocks 142. In an alternative, one continuous potting block extends around the entire periphery of a module. In other alternatives, the brace 114 is omitted or expanded. For example, a brace 114 may define some or all of a top or bottom of a potting block 142.

The mold base 112 is intended to facilitate forming the potting blocks 142 in a centrifuge. A central post 116 receives the shaft of a motor that extends outwards from the base of a centrifuge. In the example shown, the motor spins the mold base 112 in a horizontal plane while liquid potting compound is added to the mold base 112. The liquid potting compound travels, in part, through ducts 118. After the liquid potting compound solidifies, the motor can be turned off. Alternatively, the potting can be done statically. In this case, the mold base is held in a horizontally plane and liquid potting compound is poured into a section of the mold base 112 temporarily located below the central post 116. After the potting compound in this section of the mold base 112 hardens, the mold base can be rotated to add potting compound to another section of the mold base 112.

Figure 17:
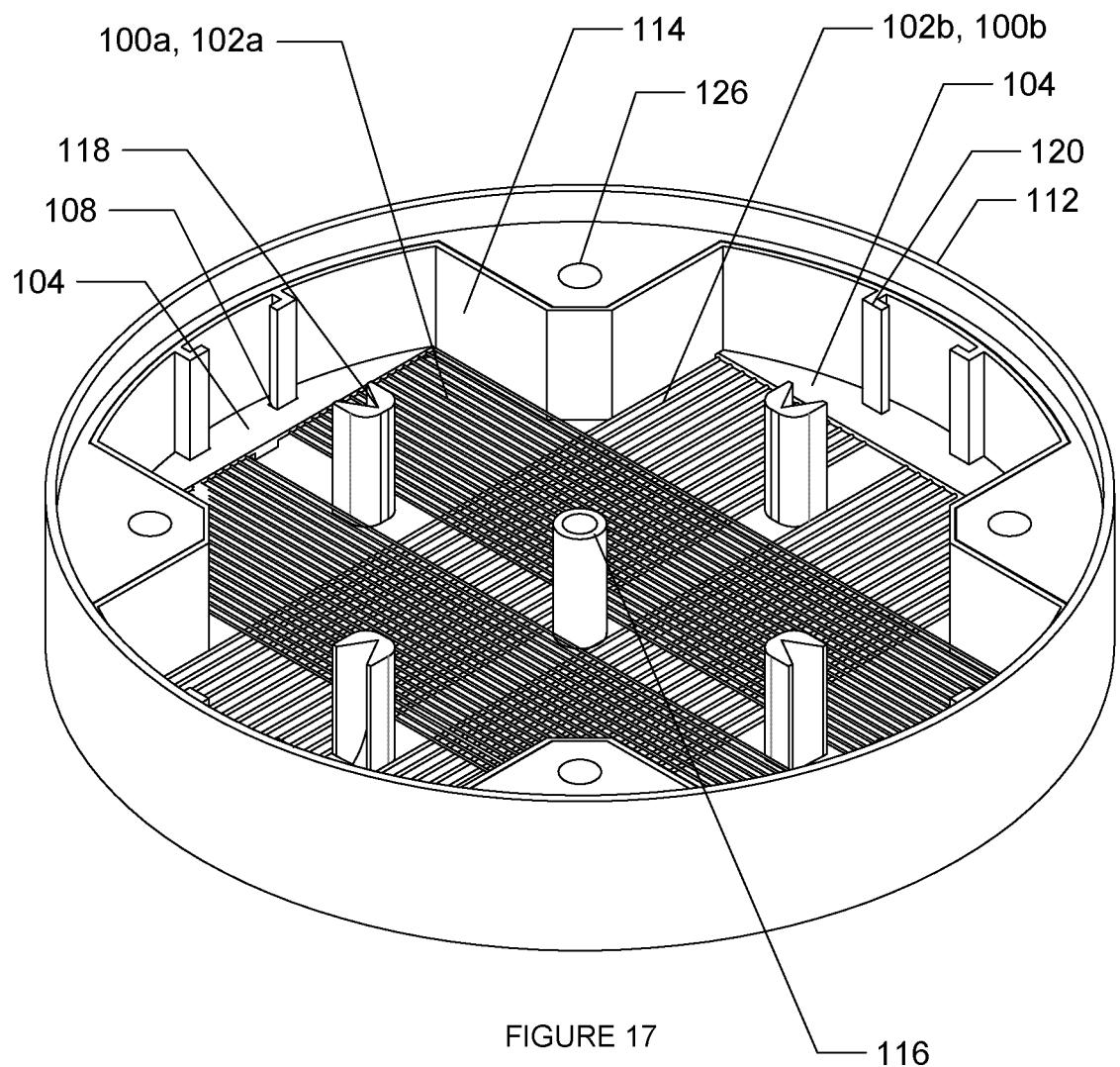
FIG. 17 is a schematic isometric view of the mold base of FIG. 16 with two mats of FIG. 15 inserted into it.

FIG. 17 shows the mold base 112 with the brace 114 and two mats 102 inserted into it. Splines 120 in the brace 114, or alternatively in the mold base 112, receive the keys 108 of the mats 102 to help restrain the mats 102. A first mat 102*a* is placed in the bottom of the mold base 112. A second mat 102*b* is placed over the first mat 102*a*. Although not shown to simplify the drawing, another first mat 102*a* is then placed over the second mat 102*b* and then another second mat 102*b* is added. This pattern is repeated until a sufficient number of mats 102 have been placed in the mold base to substantially fill the height available within the mold base 112. In the example shown, the mold base 112 has four sections and the first mats 102*a* extend in a first direction and the second mats 102*b* extend in a second direction perpendicular to the first direction. In other examples, the mold base might have 2 sections or more than 4 sections. In other examples, the hollow fiber membranes 100 of the first mat 102*a* may be woven together with the hollow fiber membranes 100 of the second mat 102*b*. In the example shown, the first mats 102*a* contain perfusion membranes 100*a* while the second mats 102*b* contain gas transfer membranes 100*b*. Either a first mat 102*a* or a second mat 102*b* can form the top or bottom layer. In other examples, all of the of the mats 102 contain the same type of membranes.

Figure 18:
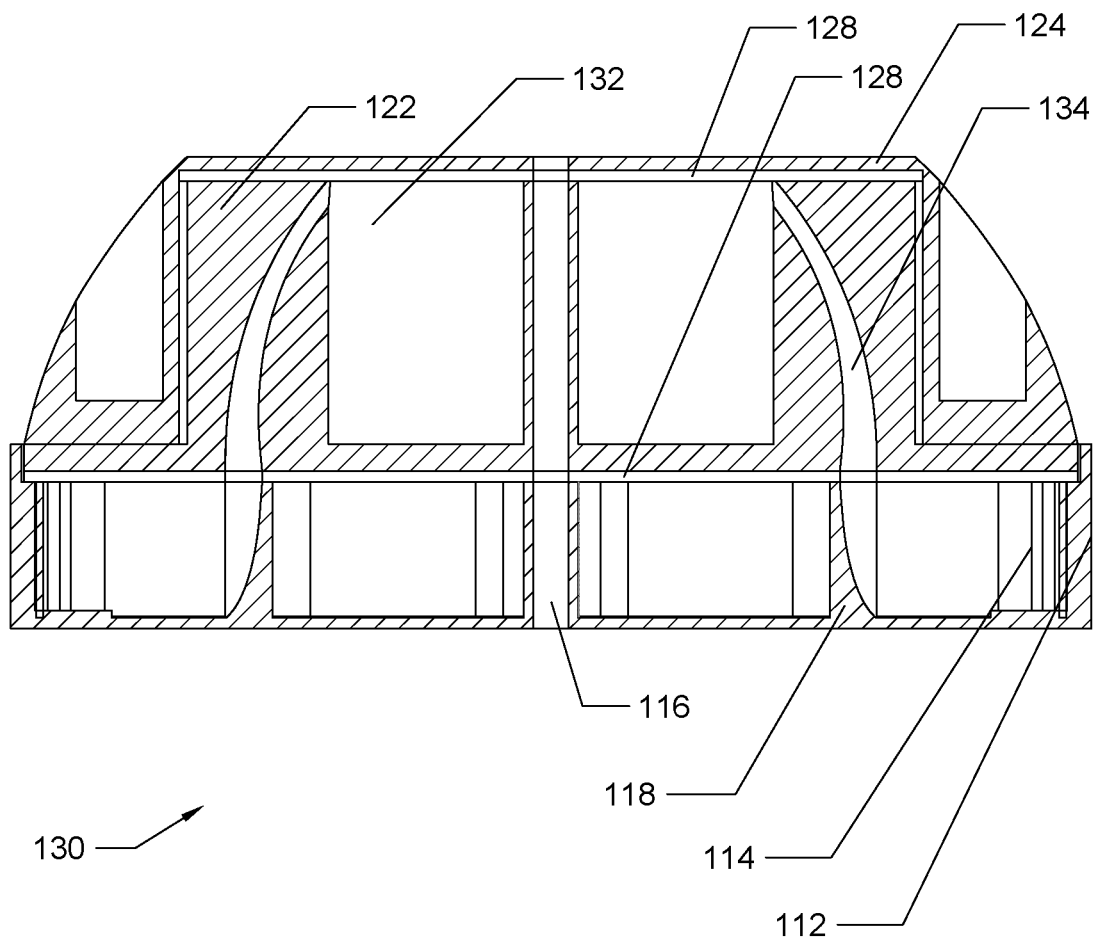
FIG. 18 is cross section of a mold including the mold base of FIG. 17.

FIG. 18 shows a mold 130, which in this example includes the mold base 112, a reservoir layer 122 and a balance layer 124. These components may be temporarily assembled together by way of bolts passing through holes (not visible in FIG. 18) through the reservoir layer 122 and the balance layer 124 into threaded holes 126 (visible in FIG. 17 for example) in the mold base 112. Optionally, one or more surfaces of different components of the mold 130 may be separated from each other by gaskets 128. Optionally, some or all of a gasket 128 that will contact the potting compound may become a part of a module 140 produced in the mold 130. In use, a number of mats 102 are placed in the mold base 112. The reservoir layer 122 is placed on the mold base 112. The bottom of the reservoir layer 122, optionally with an associated gasket 128, covers one or more casting areas within the mold base 112. Liquid potting compound is placed in reservoir 132. The balance layer 124 is placed on the reservoir layer 122. The balance layer 124 encloses the reservoir 132 and is optionally used to balance the entire mold 130. The balance layer 124 and the reservoir layer 122 are then bolted to the mold base 112. The mold 130 is then placed on a centrifuge table and fastened to the shaft of a motor (or shaft driven by a motor) extending though the central post 116. When the shaft is rotated at sufficient speed, centrifugal force causes the liquid potting material to flow out of the reservoir 132, through passages 134 in the reservoir layer 122 and the ducts 118, and into potting areas of the mold 130. The mold 130 is rotated until the potting material has gelled or more completely solidified. After the potting material has sufficiently hardened, the mold 130 is dis-assembled and the resulting module 140 may be removed. In the example illustrated, the mold base 112 has four potting areas, one in an outer region of each of its four sections. Other arrangements of potting area are also possible. For example, a mold may have two opposed potting areas at opposite ends of a mold. In another example, a mold may have a single potting area extending around the entire periphery of the mold.

Figure 19:
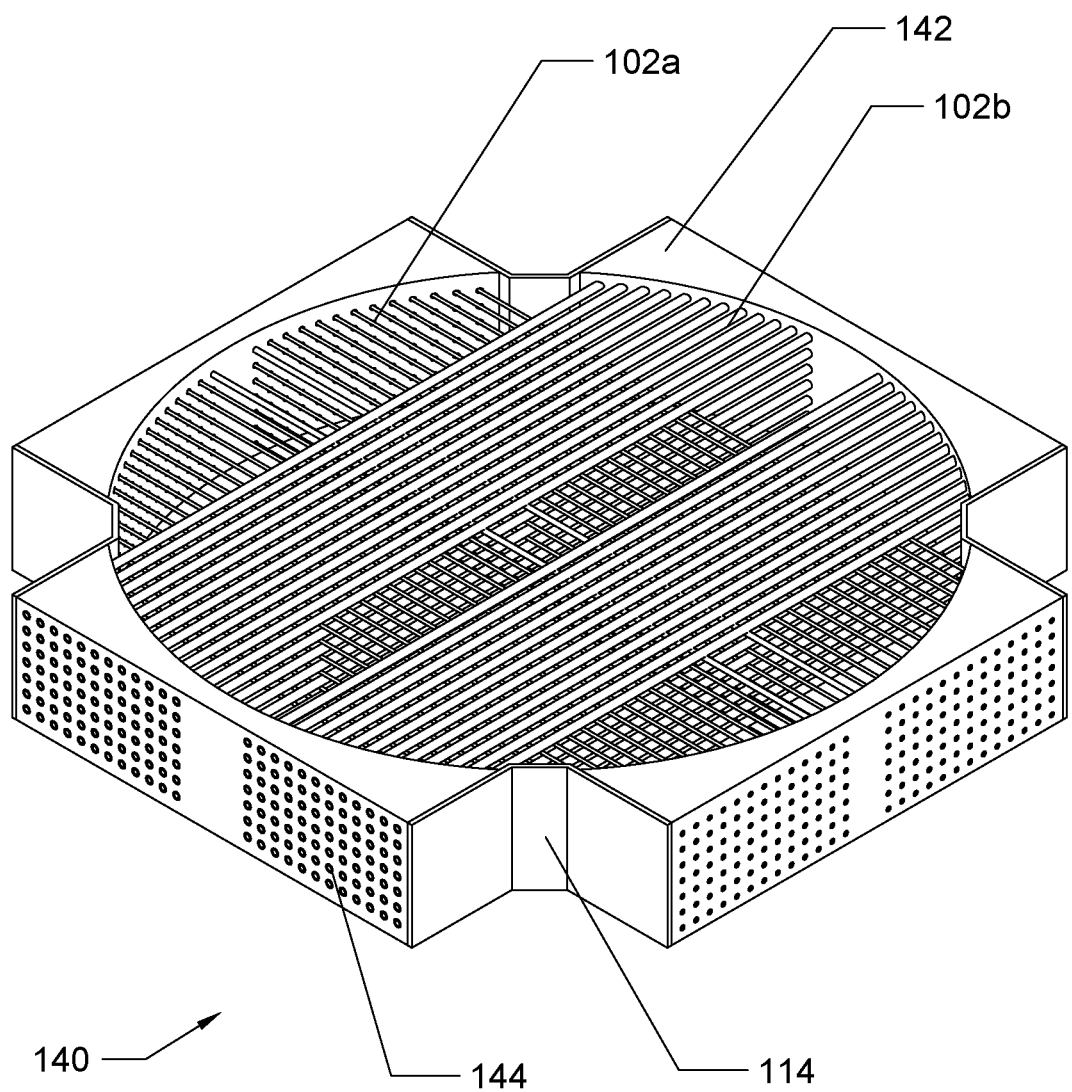
FIG. 19 is an isometric drawing of a module produced in the mold of FIG. 18 after some post processing steps.

FIG. 19 shows a module 140 produced in the mold of FIG. 18 after some post processing steps. Four potting blocks 142 were formed of potting compound that was distributed into the potting areas of the mold base 112 and solidified there. A radially outward portions of each potting block 142 is cut away to expose the lumens at open ends 144 of the hollow fiber membranes 100. Portions of the brace 114 are removed in this cutting operation, but other portions of the brace 114 remain to connect the potting block 142 together.

FIG. 20A shows a quarter side view of parts of reactor 150 made with multiple modules 140. In the example shown, the reactor 150 has three modules 140. However, an alternative reactor 150 might have one, two or more than three modules 140. The inter-capillary spaces of the modules 140 are in liquid communication with each other and collectively form one continuous plenum inside the reactor 150. The number of modules 140 may be sufficient so that the height of the plenum is 50% or more, 100% or more or 200% or more of the (average) length of the hollow fiber membranes 100 in one or both of the first mats 102*a* and the second mats 102*b*.

The reactor 150 also includes a top 154 and a base 156. The modules 140 can be sealed together and to the top 154 and the base 156 by an adhesive or through gaskets 152. If gaskets 152 are used, they may be compressed by placing the reactor 150 in a frame (not shown) or placing bolts through the reactor 150. The base 156 contains a well 158 with a mixer 160, shown also in FIG. 20C. The mixer 160 is driven by a shaft 162, which extends upwards through the reactor 150 and out through the top 154. The mixer 160 can be used, if necessary, to re-suspend cells that have settled in the well 158 or to mix growth media in the plenum. The top 154 includes one or more fittings 164 that can be used, for example, to add growth media to the plenum, to remove growth media from the plenum, to drain the reactor 150, to harvest cells or cell products, or to vent a gas headspace in the reactor 150.

FIGS. 20A and 20C show the ends 144 of the hollow fiber membranes 100 exposed. However, in use, these ends 144 are covered with headers or manifolds 151 as shown in FIG. 20C, which is optionally connected to the sides of individual modules 140 or to sides of the reactor 150 as a whole. The headers and manifolds allow fluids to flow into and out of the mats 102.

In the examples of FIGS. 15-20, the hollow fiber membranes 100 are optionally not coated or functionalized with a responsive material. However, a responsive material may be added to the hollow fiber membranes 100 of one or both of mats 102*a* or 102*b*.

Figure 21A:
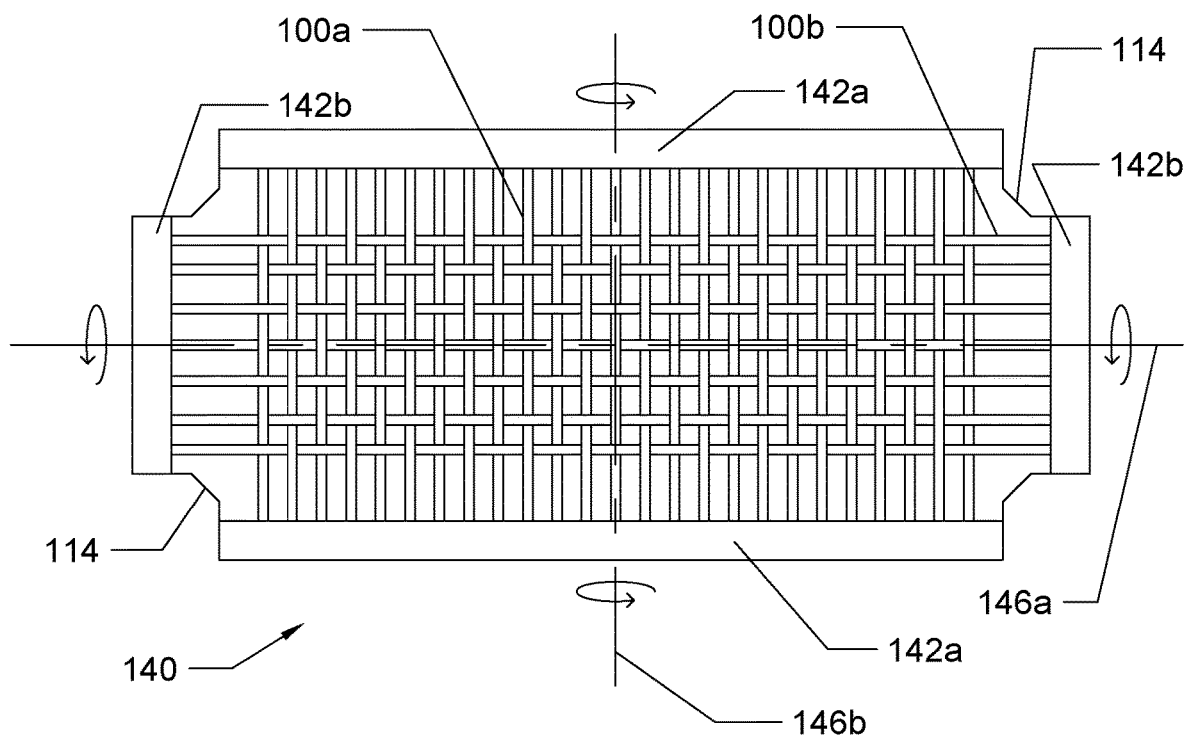
FIG. 21A shows another module being potted by way of centrifugal potting around central axes of the module.

As shown in FIG. 21A, a module 140 can be made in a shape other than square, for example a generally rectangular shape as shown. In this example, the module is also made with potting blocks 142 that are not arcuate in the plan view shown. This can be done by potting the module statically, one side at a time, similarly to the method described for the embodiments of FIGS. 1-8. Alternatively, the module 140 can be centrifuged but around a central longitudinal axis 146*a* to make the two longer potting blocks 142*a* and optionally around a central transverse axis 146*b* to make the two shorter potting blocks 142*b*. The module 140 is encased in a suitable mold, for example a horizontally split aluminum or stainless steel mold with a suitable potting material reservoir and passages.

Figure 21B:
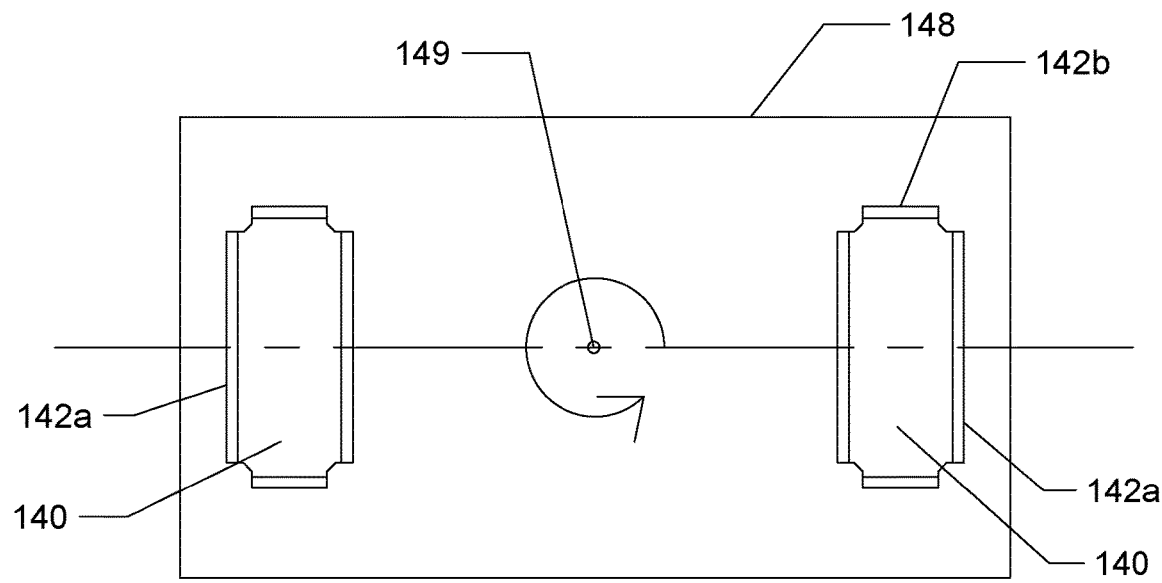
FIG. 21B is a schematic representation of another module being potted by way of centrifugal potting on a spinning platform.

In another alternative, shown in FIG. 21B, a rectangular module 140 is made with two longer potting blocks 142*a* that are arcuate. However, the radius of the arc is increased by spinning the modules 140 in pairs (or evenly spaced in numbers more than two) on a spinning platform 148. The spinning platform 148 rotates around a spinning axis 149 that is perpendicular to the spinning platform. The distance between the spinning axis 149 and the potting block 142 being molded may be twice or more than the length of the potting block 142 being molded. The module 140 is placed in a suitable mold (not shown) while being spun. The shorter potting blocks 142*b* can be made on the same spinning platform 148 are as described in relation to FIGS. 15-20.

As indicated in FIGS. 21A and 21B, a rectangular module 140 can have gas transfer membranes 100*b* that are longer than perfusion membranes 100*a*. A rectangular module 140 can be further processed and stacked to create a reactor 150 as described in relation to FIGS. 15-20. Optionally, a square module 140 can also be potted by either of the methods shown in FIGS. 21A and 21B. While the method of FIG. 21B provides only one potting block 142 per module 140 at a time, four or more modules 140 can be potted on the same spinning platform 148 to recover or even increase manufacturing process efficiency.

Figure 22A:
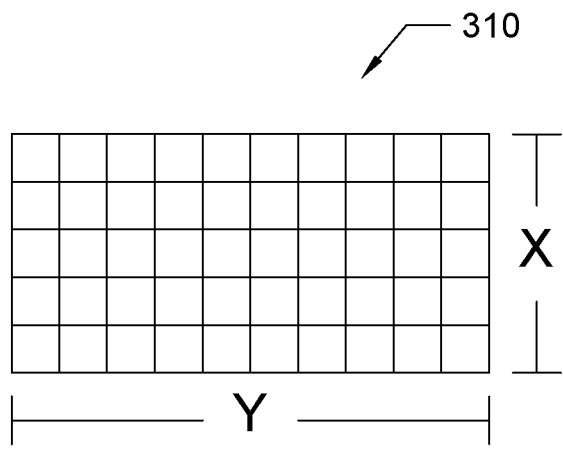
FIGS. 22A, 22B and 22C show alternative arrangements of membranes in an X-Y plane of a reactor.
Figure 22B:
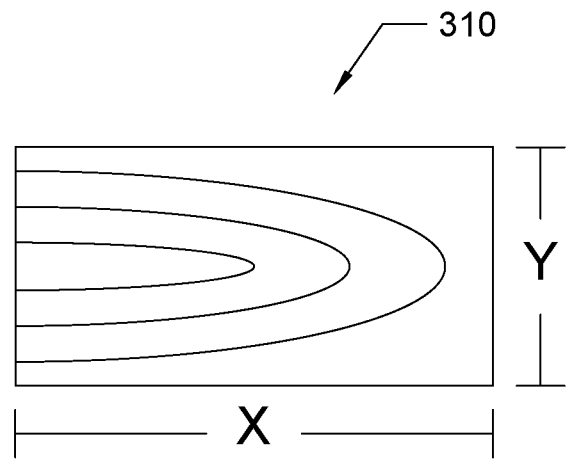
Figure 22C:
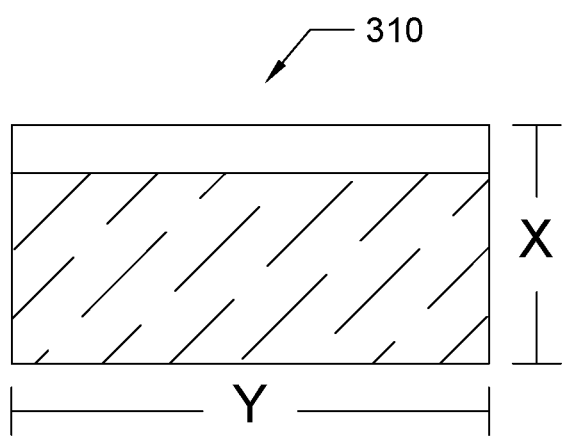
Figure 22D:
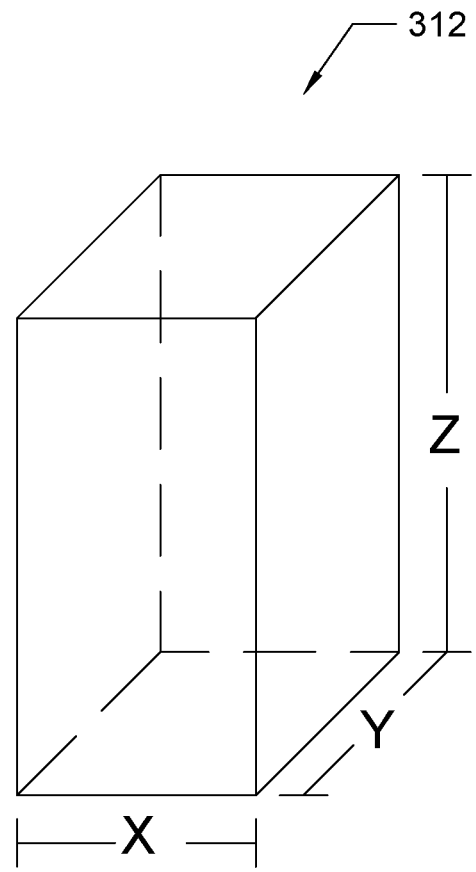
FIG. 22D shows the X, Y and Z axes of a reactor.

In the description above, the length of various reactors has been compared to the length of the membranes, which refers unless stated otherwise to the length of the perfusion membranes. If the perfusion membranes are not all of the same length, the average or mean length can be used. Alternatively, the length of the perfusion membranes may be determined by dividing the total surface area of all of the perfusion membranes by the number or perfusion membranes, and determining the length of a membrane that would have the same surface area. The length of the gas transfer membranes may be determined in the same way. In FIGS. 22A, 22B, 22C, to establish a frame of reference, the membranes are located in an X-Y plane 310 and the length of the reactor is in a Z direction. The word "plane" is not used herein according to a precise geometrical definition (by which a plane has no thickness) but instead includes three-dimensional shapes bounded by two closely (i.e. 20 mm or less or 10 mm or less) spaced planes, such that a plurality of membranes could be located between the closely spaced planes. In FIG. 22A, X is the direction of second liquid media flow and in which the length of perfusion membranes may be measured if the perfusion membranes are within about 20 degrees of variation in either direction from the grid lines shown. Y is the direction of gas flow and in which the length of gas transfer membranes may be measured in FIG. 22A if the perfusion membranes are within about 20 degrees of variation in either direction from the grid lines shown. In FIG. 22B membranes, for example perfusion membranes, travel in mixed directions the plan X-Y. The length of the perfusion membranes can be deemed to be the average, mean or calculated length as described above. In FIG. 22C, flat sheet membranes are located in the X-Y plane. The length of the flat sheet membrane can be measured in the X or Y direction according to which axis the primary direction of gas or liquid flow in the membrane is closest to, and which flow is relevant to the measurement. In all three examples, as shown in FIG. 22D, the size of the reactor can be modified by extending the reactor in the Z-direction without modifying the X-Y plane. In the examples illustrated, the X-Y planes are rectangular. In other examples, the X-Y plane may be circular, oval, square, a polyhedral or another shape. Regardless of the shape of the X-Y plane or the orientation of membranes in the X-Y plane, each reactor may be as long or more, or twice as long or more, in the Z-direction as the length and/or width of a square having the same cross-sectional area as the X-Y plane.

FIG. 23C shows a linear reactor 350 wherein the length of the reactor is parallel with the membranes 100. In this example, gas transfer membranes 100b are also provided parallel with perfusion membranes 100a. While transverse arrangements are preferred, wherein the gas transfer membranes are oblique to the perfusion membranes, a linear reactor may also be used particularly for a reactor with a small volume. Adding gas transfer membranes 100b may provide an improved distribution of oxygen over the length of the linear reactor 350 and/or allow the linear reactor 350 to be longer than it could be with only perfusion membranes 100a. In one operating mode, oxygenated second liquid media flows into a liquid inlet 352 at one end of the linear reactor 350 while air or another gas flows into a gas inlet 356 at the opposite end of the linear reactor 350. After passing through perfusion membranes 100a, second liquid media is removed through liquid outlet 354. After passing through gas transfer membranes 100b, gas is removed through gas outlet 358. The second liquid media and gas thereby flow counter-current to each other. The downstream end of the perfusion membrane substantially overlaps (i.e is within 10 mm of) the gas transfer membrane, in particular its upstream end. The same overlap occurs in the reactors with oblique perfusion and gas transfer membranes. In this way, the maximum rate of oxygen transfer from the gas transfer membranes 100b is provided at the opposite end of the linear reactor 350 from where the maximum rate of oxygen transfer from perfusion membranes 100a is provided. This may help to provide more nearly even growing conditions in the linear reactor 350.

The linear reactor 350 is made in this example by laying hollow fiber membranes 100 onto adhesive strips 230 as shown in FIG. 23A. The adhesive strips 230 are then rolled into a spiral as shown in FIG. 23B. Referring to FIG. 23C, the ends of the gas transfer membranes 100b are then closed and sealed in potting material 16, which may flow around the outer two of the adhesive strips 230 at the ends of a pipe 232 that forms a shell of the linear reactor 350. The ends of the pipe 232 are then cut through the potting material 16, which also opens the ends of the gas transfer membranes 100b as in a conventional cylindrical module potting technique. Caps 238 are attached to the ends of the pipe 232.

Thereafter, a fugitive material such as a glycerin gel is injected through the liquid inlet 352. A layer of potting material 16 can then be injected through a hole (not shown) in the side of pipe 232, for example in a layer that covers the inner two adhesive strips 230 with ends of the perfusion membranes 100b located in the fugitive material. When this layer of potting material 16 solidifies, one end of the perfusion membranes 100a are potted and hole that was used to inject it is also sealed. The fugitive material can then be flushed out through liquid inlet 352. The tube 232 is then inverted and this procedure is repeated to pot the other ends of the perfusion membranes 100a using liquid outlet 354. Alternatively, the perfusion membranes 100a can be potted simultaneously by way of centrifugal potting.

The features of exemplary reactors described above can be selected and mixed to produce sub-combinations of the features of a reactor or combinations of one or more features of one reactor with one or more features of other reactors.

Experimental Examples

Modeling Experiments—Transfer of Oxygen Through Perfusion and Gas Transfer Membranes The transfer of oxygen from a 30 cm long hollow fiber perfusion membrane to a population of *E. coli* growing in a tubular extra-capillary space (ECS) around the membrane was modeled in a COMSOL computer simulation. In the module, a perfusion membrane is fed with nearly oxygen saturated (7 mg/L $O_2$) aqueous media before it enters the capillary (inner membrane) space of the membrane. The membrane is assumed to have a porosity of 0.1 based on inspection of SEM images of a sample 50 kDa MWCO polysulfone membrane. The permeability of the same samples membrane was measured and used as the permeability input value in the model.

The module assumes that there is laminar flow of the aqueous media through the capillary space of the membrane. The transport of DO is assumed to happen by diffusion and convection in the ECS. The transport of DO through the walls of the membrane is assumed to happen by diffusion. Darcy's model is used to model the transport of dissolved oxygen (DO) through the porous walls. Monod's kinetic model is used to model *E. coli* growth in the ECS. Input parameters are given in Table 1 below. As a boundary condition, all *E. coli* are contained within the ECS.

TABLE 1

| Parameter | Input Value |
| --- | --- |
| Hollow fiber inner radius | 0.15 mm |
| Hollow fiber wall thickness | 0.25 mm |
| Hollow fiber length | 30 cm |
| ECS width | 0.32 mm |
| *E. coli* death constant | $2.78*10^{-51}$ $s^{-1}$ |
| DO diffusivity at 37° C. | 3.99 $cm^2$/s |
| *E. coli* diffusivity at 37° C. | $1*10^{-12}$ $m^2$/s |
| Monod constant | 0.31 kg/$m^3$ |
| Yield coefficient | 0.49 |
| Maintenance constant for *E. coli* | 0.003 $s^{-1}$ |
| Max specific growth | $1.81*10^{-4}$ $s^{-1}$ |
| Inlet flow rate | 4.3 mL/min |
| Operating temperature | 37° C. |
| Operating pressure | 101 kPa |
| Initial DO concentration in ECS | 0.22 mol/$m^3$ (7.04 mg/L) |
| Initial *E. coli* | 0.5 kg/$m^3$ |
| Porosity | 0.1 |
| Permeability | $1.469*10^{-10}$ $m^2$ |

Figure 24:
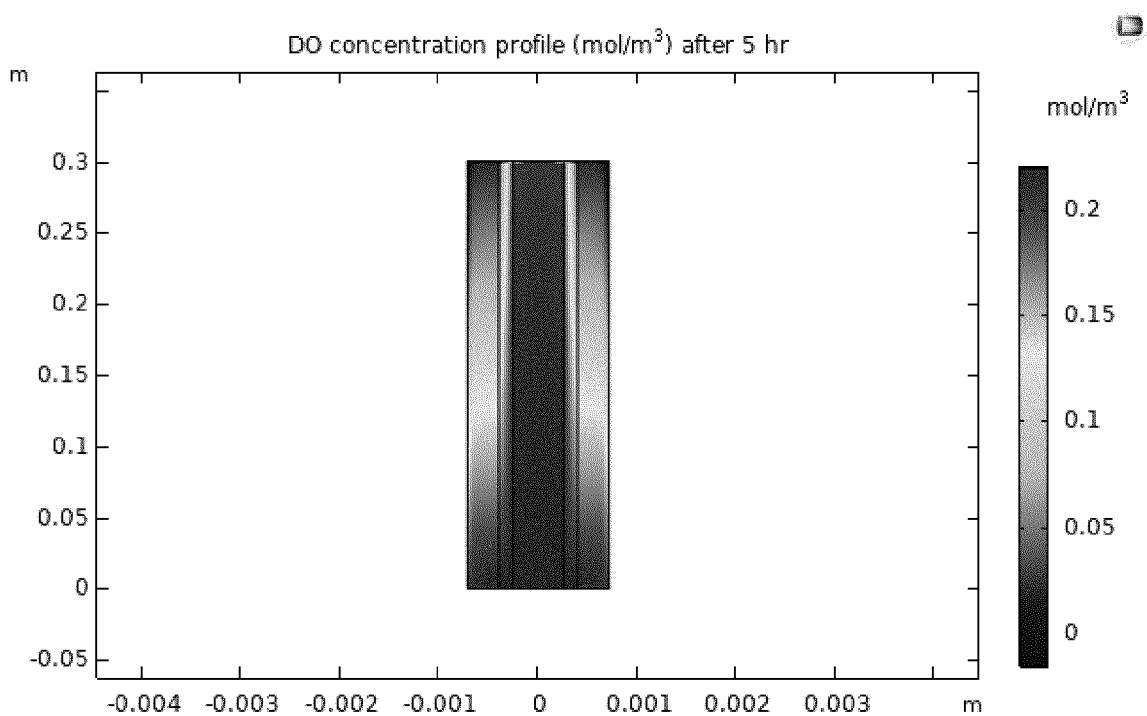
FIG. 24 shows the dissolved oxygen content in an around a perfusion membrane during in a modeling experiment.

The results of a simulation run are shown in FIG. 24. FIG. 24 shows the dissolved oxygen concentration in the ECS at 18000 seconds (5 hours). The upstream end of the ECS is still aerobic due to oxygen transferred from the oxygen saturated liquid media flowing through the perfusion membrane. However, the dissolved oxygen (DO) concentration declines along the length of the ECS. In particular, at least the last 5 cm of the downstream end of the ECS has fallen below 2 mg/L (0.0625 mol/$m^3$) DO, which is often cited as the threshold of hypoxia. Accordingly, if aerobic microorganisms were being grown (rather than *E. coli* which is a facultative anaerobe) with a similar growth rate, the modeled reactor would have reached the limits of operation after less than 5 hours.

Measurement of $k_La$ for Reactors of Various Configurations $k_La$ is a volumetric mass transfer coefficient used to describe the efficiency of oxygen transfer with a given set of conditions. $k_La$ is frequently used to compare bioreactors with different process conditions or geometries. Referring to Table 1 of International Publication WO 2005108549A1, $k_La$ for commercial stirred tank reactors range from 0.00003 to 0.007 min$^{-1}$ when growing mammalian cells and 0.02 to 0.4 min$^{-1}$ when growing microbial cells. The oxygen demands of mammalian cells are typically much lower than the oxygen demands of microbial cells. However, the primary difference between mammalian cells and microbial cells is that mammalian cells are less tolerant of shear and other forces and die when exposed to high impeller speeds and gassing rates in stirred tank reactors. Thus, an increase in $k_La$ above the values used to grow mammalian cells in commercial reactors would be beneficial, but only if it can be achieved without the high impeller speeds and other conditions of microbial stirred tank reactors.

In trial 1, a single cartridge reactor generally as shown in 7A was made having only gas transfer membranes. The reactor had 153 dense walled PDMS hollow fiber membranes, each about 5 cm long (as measured within the ECS), with an outside diameter of 0.3 mm. The reactor had an extra-capillary space (ECS) of 28 mL. The ECS was initially filled with deoxygenated water and there was no inflow or outflow of water from the ECS during the experiment. Room temperature air was pumped through the hollow fiber membranes at 0.3 L per minute (Lpm). The gas outlet of the cartridge was open to atmosphere. Dissolved oxygen (DO) readings in the ECS were recorded over a period of 17 minutes. The kLa of this reactor, calculated from the DO readings, was 0.0492 min$^{-1}$.

In trial 2, another single cartridge reactor generally as shown in 7A was made having only gas transfer membranes. This reactor had 48 polypropylene hollow fiber porous membranes, each about 5 cm long (measured within the ECS), with an outside diameter of 0.5 mm. The membranes were manufactured for use in pressure-driven ultrafiltration but were washed and dried to remove pore-preserving agents. The membranes then had dry pores and functioned as gas transfer membranes. The reactor had an extra-capillary space (ECS) of 28 mL. The ECS was initially filled with deoxygenated water. Room temperature air was pumped through the hollow fiber membranes at 0.3 L per minute (Lpm). The gas outlet of the cartridge was open to atmosphere and there was no inflow or outflow of water from the ECS during the experiment. Dissolved oxygen (DO) readings in the ECS were recorded over a period of 70 minutes. The kLa of this reactor, calculated from the DO readings, was 0.0272 min$^{-1}$.

In trial 3, the conditions in trial 2 were duplicated but deoxygenated water was pumped through the ECS at 4.3 mL/min. The continuous dilution of oxygenated water in the ECS produced a drop in the $k_La$, relative to trial 2, to 0.0032 min$^{-1}$. In trial 4, the conditions of trial 3 were duplicated but the gas outlet of the cartridge was closed and room temperature air was pumped into the gas transfer membranes at 0.16 Lpm. The $k_La$ increased, relative to trials 2 and 3, to 0.434 min$^{-1}$.

In trial 4, another single cartridge reactor generally as shown in 7A was made having only perfusion membranes. This reactor had 46 polysulfone hollow fiber membranes, each about 5 cm long (measured within the ECS), with an outside diameter of 0.8 mm and a molecular weight cut-off (MWCO) of 50 kDa. The reactor had an extra-capillary space (ECS) of 28 mL. The ECS was initially filled with deoxygenated water and there was no inflow or outflow of water from the ECS during the experiment. Oxygenated water (98% DO) was pumped through the lumens of the hollow fiber membranes at 4.3 mL/min. Dissolved oxygen (DO) readings in the ECS were recorded over a period of 60 minutes. The kLa of this reactor, calculated from the DO readings, was 0.0081 min$^{-1}$. In similar experiments, multiple cartridges were connected together in series to simulate reactors with 20 cm (trial 5) and 30 cm (trial 6) perfusion membranes. Oxygenated water (98% DO) was pumped through into the first reactor in the series at 4.3 mL/min. The $k_La$ of the simulated 20 cm reactor was 0.0070 min$^{-1}$. The $k_La$ of the simulated 30 cm reactor was 0.0023 min$^{-1}$.

In trial 7, another single cartridge reactor generally as shown in 7A was made having both perfusion membranes and gas transfer membranes. The perfusion membranes were 46 polysulfone hollow fiber membranes, each about 5 cm long (measured within the ECS), with an outside diameter of 0.8 mm and a molecular weight cut-off (MWCO) of 50 kDa. The gas transfer membranes were 306 dense walled PDMS hollow fiber membranes, each about 5 cm long (as measured within the ECS), with an outside diameter of 0.3 mm. The gas outlet of the reactor was open to the atmosphere. The reactor had an extra-capillary space (ECS) of 28 mL. The ECS was initially filled with deoxygenated water and there was no inflow or outflow of water from the ECS during the experiment. Oxygenated water (98% DO) was pumped through the hollow fiber membranes at 0.5 mL/min. Air flowed through the gas transfer fibers at 0.5 Lpm. Dissolved oxygen (DO) readings in the ECS were recorded over a period of 2 minutes. The kLa of this reactor, calculated from the DO readings, was 2.6 min$^{-1}$.

As indicated by these results, the use of gas transfer membranes produced about an order of magnitude increase in $k_La$ compared to flowing oxygen-saturated water through perfusion membranes. The perfusion membranes were capable of producing $k_La$ values similar to commercially available reactors for culturing mammalian cells. The gas transfer membranes were able to produce $k_La$ values comparable to, or in the case of trial 7 better than, commercially available reactors for culturing mammalian cells. Further, the $k_La$ produced using gas transfer membranes with the outlet closed, even while flowing deoxygenated water through the ECS, suggests that an increase in $k_La$ beyond what is currently used in microbial stirred tank reactors could be available by using pressurized gas transfer membranes.

Vero Cell Shedding from Polyethersulfone (PES) Membranes

Polyethersulfone (PES) membranes were functionalized with PNIPAAm by way of surface initiation by directed ortho metalation (lithiation) followed by atom transfer radical polymerization (ATRP). The functionalization of PS, PES and PVDF membranes is described more completely in copending U.S. application 62/856,315, Sulfonated and Halide Membranes with Thermo-Responsive Surface Treatment, which is incorporated herein by reference.

In this example, to perform the lithiation, 70 mg of PES membranes are soaked in ethanol for 2 hours. 60 mL of diethyl ether is placed into a Schlenk flask and purged with nitrogen for 15 min. The membranes are added to the Schlenk flask and purged with nitrogen for 15 min. 0.237 ml of butyllithium (Bu-Li) is added under inert atmosphere with capped condenser. The reaction is stirred for 2 hours in a water bath of around 17° C. 0.88 ml of 3-(chloromethyl) benzoyl chloride is added stirred for 1 hour. The reaction is quenched with 40 ml of ethanol. The membranes are removed, washed thoroughly and dried in air.

To functionalize the membranes, 25.38 mg Cu(1)Cl, 82.859 mg 2,2'-Bipyridyl, and 0.604 g NIPAA are added in a dry Schlenk flask. 30 ml of ethanol solution in DI water (50:50 v/v) is added. The surface initiated membranes are added into the Schlenk flask. The flask is purged with nitrogen for 15 min. A capped condenser is added and the reaction is stirred for 3 hours. The membranes are removed, washed thoroughly, and dried in air.

The contact angle of the untreated PES membrane has measured and was about 65° at both 25° C. and 60° C. The contact angle of the PES-PNIPAAm membrane made as described above was 24° at 25° C. and 42° at 60° C. Table 1 gives the flux of the membrane in DI water before and after functionalization.

TABLE 1

| Membrane | Flux (ml h$^{-1}$ m$^{-2}$) at 25° C. | Flux (ml h$^{-1}$ m$^{-2}$) at 40° C. |
| --- | --- | --- |
| PES | 31400 | 32154 |
| PES-PNIPAAm | 14200 | 5846 |

Samples of PES (without PNIPAAm) and PES-PNIPAAm (made as described above) were sterilized in an autoclave and cut into pieces of equal size. The cut samples were placed in some of the wells of a 96-well plate (there were less than 96 samples). 20,000 Vero cells were added in each well containing a membrane sample, along with a cell culture media of DMEm/F12+10% FBS2. After 24 hours of cell growing time, the plate was placed in a refrigerator at 4° C. for 10 hours. A first cell count of the media was performed to assess the number of cells shed from the membranes in the refrigerator. The wells were then trypsinized and a second cell count was performed to determine if cells remained on the membranes after refrigeration.

In one pair of samples, in the first cell count (before trypsinization) about 40,000 cells were counted from the well containing the PES-PNIPAAm sample and none were counted from the well containing PES sample. In the second cell count (after trypsinization) about 100,000 cells were counted from the well containing the PES sample and none were counted from a PES-PNIPAAm sample.

E. coli Growth Results

A single cartridge reactor (Cartridge A) was made generally as shown in FIG. 7A but with perfusion membranes in both directions. The perfusion membranes were polysulfone (PS) membranes with a 0.8 mm outer diameter and 0.4 mm inner diameter. The MWCO was 50 kDa. The cartridge had 48 hollow fiber perfusion membranes each about 5 cm long. The ECS was about 5 cm long, 5 cm wide and 1 cm high. The cartridge was used to grow E. coli at a temperature of 37° C. LB was used as the liquid media in the capillary space and the ECS. The liquid media for the capillary space was oxygenated with bubbles and fed to the perfusion fibers through silicone tubing.

Another single cartridge reactor (Cartridge B) was made generally as shown in FIG. 7A but with perfusion membranes perpendicular to gas transfer membranes. The perfusion membranes were polysulfone (PS) membranes with a 0.8 mm outer diameter and 0.4 mm inner diameter. The MWCO was 50 kDa. The gas transfer membranes were polypropylene membranes with an outer diameter of 0.5 mm and inner diameter of 0.3 mm. The pores were dry with a size of 450 nm. The cartridge had 24 hollow fiber perfusion membranes and 24 hollow fiber gas transfer membranes, each about 5 cm long. The ECS was about 5 cm long, 5 cm wide and 1 cm high. The cartridge was used to grow E. coli at a temperature of 37° C. LB was used as the liquid media in the capillary space and the ECS. The liquid media for the capillary space was oxygenated with bubbles and fed to the perfusion fibers through silicone tubing to saturate it with oxygen. Air was also pumped through the gas transfer hollow fibers.

Each single cartridge reactor was seeded with a different dispersion of E. coli having an optical density to 600 nm light of approximately 0.2. For comparison, in each trial some of the dispersion used to seed the cartridge was also used to seed a shaker flask. The shaker flask was operated at 37° C. set in a rotary shaker at 225 rpm. Atmospheric air is available in the headspace of the flask but the liquid media is not replenished. Although the consumption of compounds in the liquid media might eventually limit growth in the shaker flask, it is assumed that for at least an initial period of time, possibly in the range of 12-24 hours, growth in the shaker flask is not limited by the lack of oxygen or any nutrient supplied in the liquid media. Although the results for Cartridge A are not directly comparable to the results for Cartridge B because different seed dispersions were used, each cartridge can be compared to a flask that was seeded with the same dispersion. The performance of Cartridges A and B relative to their associated flask can be used to provide a qualitative comparison of Cartridges A and B.

Figure 25:
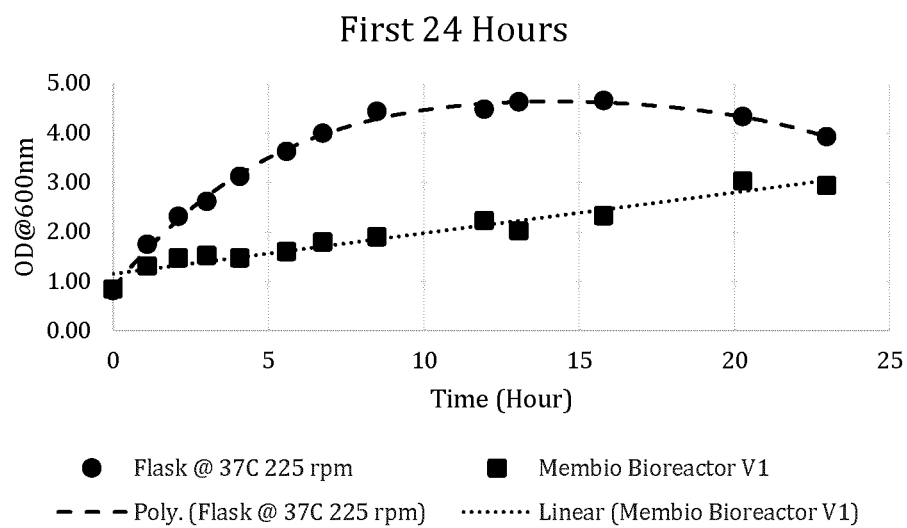
FIG. 25 shows the optical density over 24 hours within a shaker flask and a bioreactor with perfusion membranes.

FIG. 25 shows the increase in optical density (600 nm) in cartridge A (Membio Bioreactor V1) compared to the flask seeded from part of the same initial dispersion of E. coli over 23 hours. As indicated in FIG. 25, initial growth in the flask was faster than in the perfusion membrane bioreactor indicating that the flask initially had better oxygen transfer. However, whereas growth in the flask was declining at 23 hours, growth in the perfusion membrane bioreactor was increasing. The experiment with the flask was terminated at 23 hours, but the perfusion membrane bioreactor continued in operation. At 173 hours, the perfusion membrane bioreactor has reached an optical density of 25.6 and was still showing an increase in population growth with time.

Figure 26:
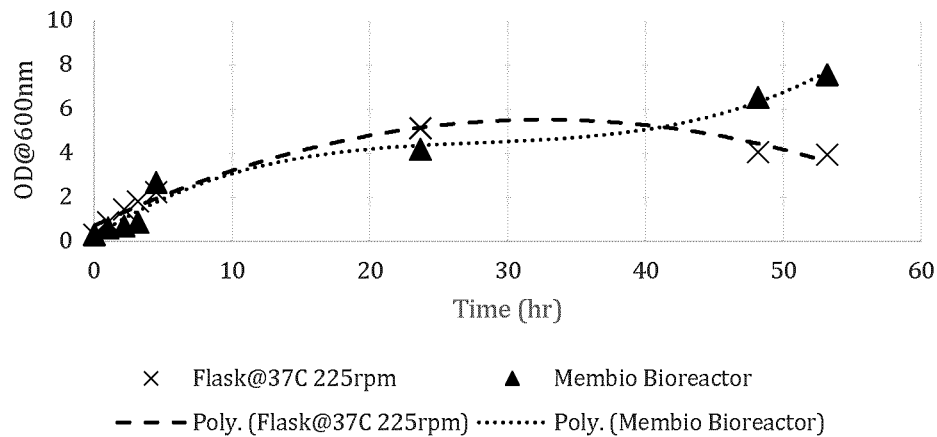
FIGS. 26 and 27 show the optical density over 53 hours and 380 hours within a shaker flask and a bioreactor with perfusion membranes and gas transfer membranes.
Figure 27:
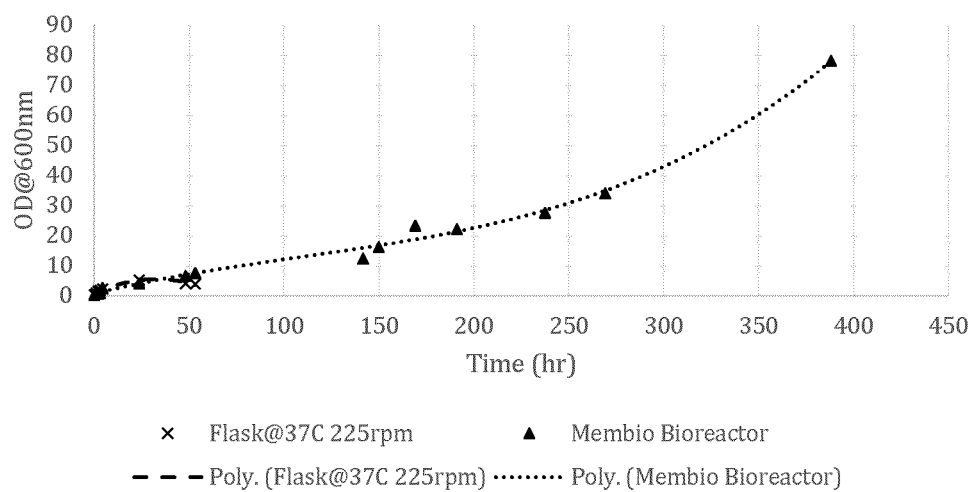

FIG. 26 shows the increase in optical density (600 nm) in cartridge B (Membio Bioreactor) compared to the flask seeded from part of the same initial dispersion of E. coli over 53 hours. As indicated in FIG. 26, initial growth in the flask was similar to initial growth in the cartridge suggesting that neither of them were nutrient limited up to about 24 hours. However, whereas growth in the flask had stopped at 53 hours, growth in the perfusion membrane bioreactor was increasing. The experiment with the flask was terminated at 142 hours at which time the optical density was still 3.9. However, as shown in FIG. 27, the cartridge continued in operation for 388 hours and reached an optical density of 78.

Further E. coli Growth Results

In another experiment, two single cartridge reactors were made generally as shown in FIG. 7A. Each cartridge had 46 hollow fiber perfusion membranes made of polysulfone (PS) membranes with a 0.8 mm outer diameter and MWCO of 50 kDa. Each cartridge also had 306 PDMS dense walled gas transfer membranes with an outer diameter of 0.3 mm. The ECS was about 5 cm long, 5 cm wide and 1 cm high. The cartridge was used to grow E. coli at a temperature of 25° C. Liquid growth media was circulated through the perfusion membranes at 5.3 mL/min using 164 cm of Masterflex silicone tubing, which is expected to oxygenate the liquid media. The gas transfer membranes where either not supplied with oxygen (Trial A) or supplied with oxygen at 0.5 L/min (Trial B). The cartridges were placed on an orbital shaker.

Figure 28:
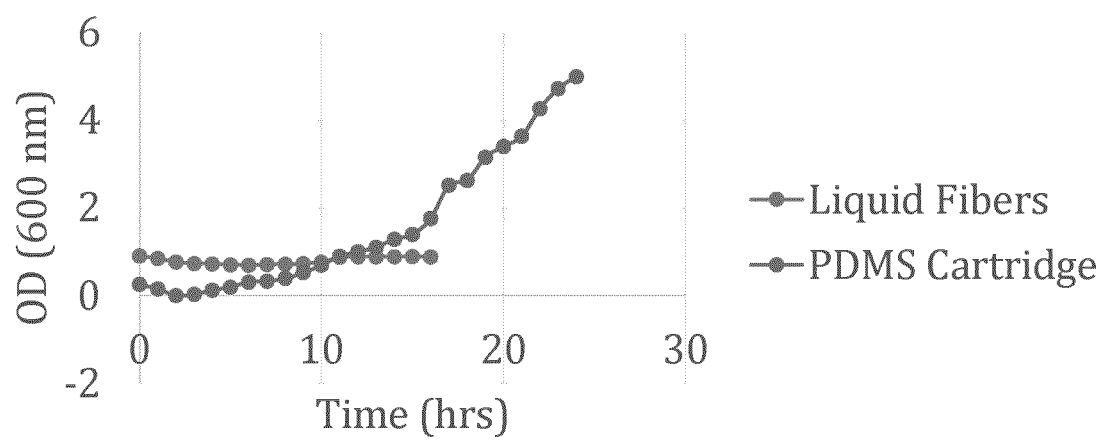
FIG. 28 shows the optical density over time for a bioreactor with perfusion membranes and a bioreactor with perfusion membranes and gas transfer membranes.

FIG. 28 shows the optical density (OD) at 600 nm in the extra-capillary space over time, which indicates the amount of *E. coli* in the reactor. In Trial A (liquid fibers), optical density did not materially increase after more than 15 hours. In Trial B (PDMS Cartridge), the optical density had increased to 5 over about 24 hours, indicating significantly faster growth of *E. coli* than in trial A.

We claim:

1. A cell culture bioreactor comprising,
a plenum to contain a growth media and growing cells;
a plurality of perfusion membranes within the plenum; and,
a plurality of gas transfer membranes within the plenum,
wherein ends of the plurality of perfusion membranes and ends of the plurality of gas transfer membranes are held in potting blocks,
and wherein the potting blocks have arcuate inner faces formed of a solidified potting compound defining portions of the plenum,
and wherein the plenum is generally cylindrical.

2. The cell culture bioreactor of claim 1 wherein the plurality of perfusion membranes are a plurality of hollow fiber membranes and the plurality of gas transfer membranes are a plurality of hollow fiber membranes.

3. The cell culture bioreactor of claim 2 wherein the plurality of perfusion membranes are oriented obliquely to the plurality of gas transfer membranes.

4. The cell culture bioreactor of claim 2 wherein the plurality of perfusion membranes are woven with the plurality of gas transfer membranes.

5. The cell culture bioreactor of claim 2 wherein the plurality of perfusion membranes are in alternating layers with the plurality of gas transfer membranes.

6. The cell culture bioreactor of claim 2 wherein the plurality of perfusion membranes are 20 cm or more in length.

7. The cell culture bioreactor of claim 2 wherein the plurality of gas transfer membranes and/or the plurality of gas transfer membranes comprises a responsive surface.

8. The cell culture bioreactor of claim 7 wherein the plurality of perfusion membranes comprises polysulfone or polyethersulfone and the responsive surface comprises NIPAAm.

9. The cell culture of bioreactor of claim 1 wherein the plenum is at least 50% as long as the plurality of perfusion membranes in a direction oblique to the plurality of perfusion membranes and wherein the membranes are arranged to provide channels perpendicular to the membranes.

10. The cell culture bioreactor of claim 1 wherein the plenum comprises a plurality of modules stacked together in a direction oblique to the plurality of gas transfer membranes, wherein each module has a plurality of layers of perfusion membranes and a plurality of layers of gas transfer membranes.

11. The cell culture bioreactor of claim 1 comprising a mixer in the plenum.

12. The cell culture bioreactor of claim 1 further comprising micro-carriers in the plenum.

13. The cell culture bioreactor of claim 1 wherein the gas transfer membranes are porous membranes.

14. A cell culture bioreactor comprising,
a plenum to contain a growth media and growing cells;
a plurality of hollow fiber perfusion membranes within the plenum; and,
a plurality of hollow fiber gas transfer membranes within the plenum;
wherein the plurality of gas transfer membranes are parallel with the plurality of perfusion membranes and wherein the plurality of gas transfer membranes are potted in first layers of potting material and the plurality of perfusion membranes are potted in second potting layers spaced apart in a direction parallel to the membranes from the first layers of potting material, wherein the second potting layers are located between the first potting layers and the plurality of gas transfer membranes pass through the second potting layers.

15. The cell culture bioreactor of claim 14 wherein the plurality of gas transfer membranes are counter-current to the plurality of perfusion membranes.

* * * * *